United States Patent [19]

Hugh et al.

[11] Patent Number: 5,792,427
[45] Date of Patent: Aug. 11, 1998

[54] CONTROLLED ATMOSPHERE INCUBATOR

[75] Inventors: Mark A. Hugh, Marietta; David V. Lohr, Beverly; Peter J. Borton, Marietta, all of Ohio

[73] Assignee: Forma Scientific, Inc., Marietta, Ohio

[21] Appl. No.: 599,150

[22] Filed: Feb. 9, 1996

[51] Int. Cl.[6] .................................................. C12M 1/36
[52] U.S. Cl. ........................ 422/109; 422/99; 435/303.1; 435/809; 49/489.1; 49/490.1; 219/407; 219/408; 219/520; 219/522; 236/3; 237/3; 392/438; 392/439; 411/34; 411/542
[58] Field of Search .............................. 422/109, 99, 104, 422/101; 435/303.1, 809; 236/316; 219/385, 400, 407, 408, 409, 412, 522, 520, 543; 392/407, 435, 438, 439; 237/R, 3, 4; 338/308, 309; 411/34, 38, 542; 49/489.1, 490.1

[56] References Cited

U.S. PATENT DOCUMENTS

| | | |
|---|---|---|
| 3,002,895 | 10/1961 | Freedman . |
| 3,576,721 | 4/1971 | Mason . |
| 3,659,079 | 4/1972 | Whittemore . |
| 3,710,074 | 1/1973 | Stewart . |
| 3,756,069 | 9/1973 | Carswell . |
| 3,797,172 | 3/1974 | Cannon ................................. 49/148 |
| 3,833,451 | 9/1974 | Wagner ................................. 161/45 |
| 3,857,757 | 12/1974 | Herrick . |
| 3,887,436 | 6/1975 | Haddad . |
| 3,929,584 | 12/1975 | Mansfield . |
| 3,948,732 | 4/1976 | Haddad . |
| 3,987,133 | 10/1976 | Andra . |
| 4,001,974 | 1/1977 | Wright ................................. 49/488 |
| 4,033,825 | 7/1977 | Haddad . |
| 4,039,775 | 8/1977 | Andra ................................. 219/385 |
| 4,336,329 | 6/1982 | Hesse . |
| 4,356,967 | 11/1982 | Lunick . |
| 4,398,091 | 8/1983 | Passaro . |
| 4,443,791 | 4/1984 | Risgin . |
| 4,457,111 | 7/1984 | Koike ................................. 49/441 |
| 4,498,330 | 2/1985 | Hosoya . |
| 4,521,147 | 6/1985 | King, Jr. et al. ........................ 411/43 |
| 4,527,807 | 7/1985 | Urbanick ................................. 277/189 |
| 4,644,698 | 2/1987 | Gerdes et al. ........................ 49/478 |
| 4,668,854 | 5/1987 | Swan . |

(List continued on next page.)

OTHER PUBLICATIONS

Revco Scientific, Revco Laboratory $CO_2$ Incubators, 1995, unpaginated.
Revco Scientific, Revco Laboratory $CO_2$ Incubators, no date, 13 p.
Revco Scientific, Revco Ultima Laboratory $CO_2$ Incubators, 1993, unpaginated.
Revco Scientific, Revco Ultima Laboratory $CO_2$ Incubators, 1992, 6 p.
Forma Scientific, Inc., Understanding Automatic $CO_2$ Control Systems, 1981, 8 p.

*Primary Examiner*—Long V. Le
*Attorney, Agent, or Firm*—Wood, Herron & Evans, L.L.P.

[57] ABSTRACT

A controlled atmosphere incubator having an interior chamber surrounded by a heated water jacket. A glass access door of the chamber is directly heated by a clear, electrically conductive coating. The door is sealed against the perimeter of the opening by a readily replaceable gasket and is field reversible due to unique hinge mounting assemblies. An easily accessed blower assembly is located within the chamber and includes a HEPA filter readily replaceable by the user from within the chamber. A filtered air exchange system is provided for limiting the maximum level of humidity in the chamber. The incubator control maintains constant power output from the blower motor so that the heat output of the motor is also constant. A voltage compensated temperature control is also provided for the heaters associated with the water jacket. Compensation for environmental conditions inside the chamber is also provided by the control for producing more accurate readings of carbon dioxide levels. When an infrared carbon dioxide sensor is used, the control provides a unique calibration method which does not necessitate the use of conventional tanks of calibration gas mixtures.

22 Claims, 10 Drawing Sheets

U.S. PATENT DOCUMENTS

| | | |
|---|---|---|
| 4,689,303 | 8/1987 | Kraft . |
| 4,701,415 | 10/1987 | Dutton . |
| 4,716,536 | 12/1987 | Blanchard . |
| 4,730,479 | 3/1988 | Pyke . |
| 4,786,784 | 11/1988 | Nikodem . |
| 4,789,283 | 12/1988 | Crawford .................................. 411/43 |
| 4,896,143 | 1/1990 | Dolnick . |
| 4,952,783 | 8/1990 | Aufderheide et al. ................... 219/528 |
| 5,005,523 | 4/1991 | Foster ........................................ 119/37 |
| 5,021,074 | 6/1991 | Kovacik . |
| 5,028,759 | 7/1991 | Finley . |
| 5,066,111 | 11/1991 | Singleton . |
| 5,090,617 | 2/1992 | Swan . |
| 5,119,467 | 6/1992 | Barsky et al. ............................ 392/439 |
| 5,161,329 | 11/1992 | Brown ........................................ 49/380 |
| 5,217,692 | 6/1993 | Rump . |
| 5,342,676 | 8/1994 | Zagdoun . |
| 5,352,414 | 10/1994 | Rothenberg . |
| 5,354,966 | 10/1994 | Sperbeck .................................. 219/203 |
| 5,416,931 | 5/1995 | Wolfenden . |
| 5,418,131 | 5/1995 | Butts . |
| 5,569,005 | 10/1996 | Millington ................................ 411/34 |

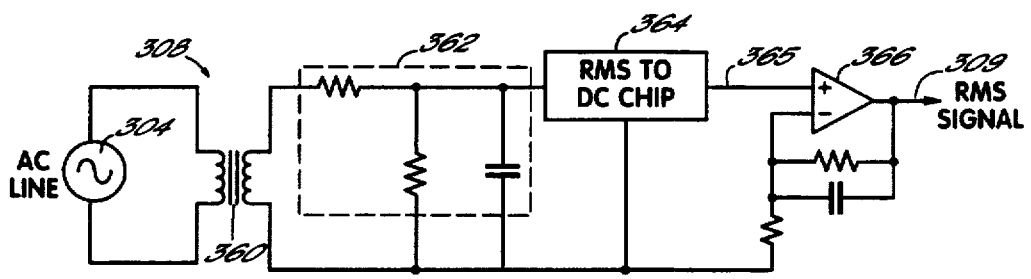
FIG. 10A
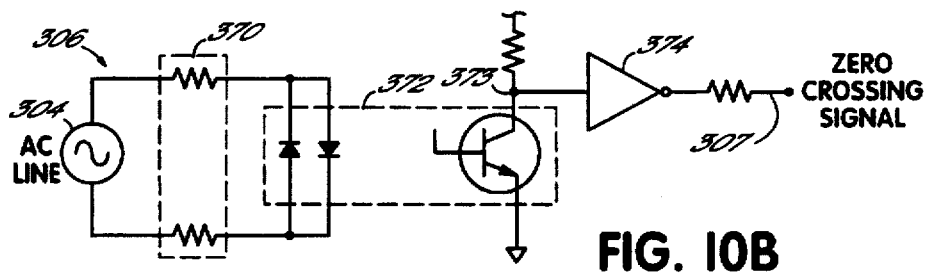
FIG. 10B
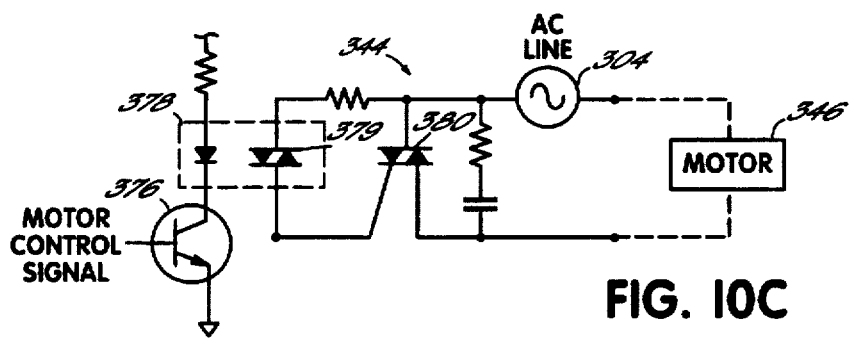
FIG. 10C
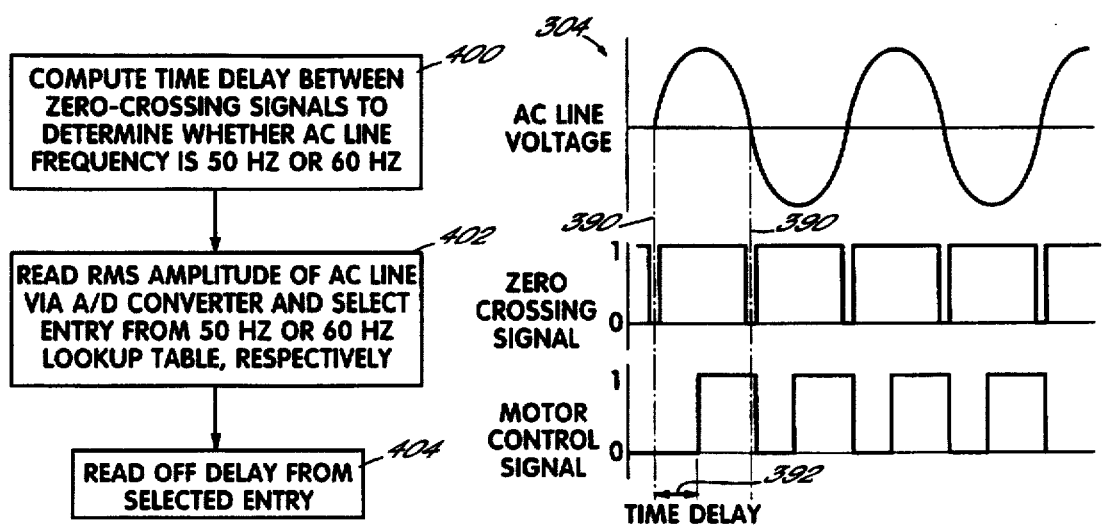
FIG. 11A
FIG. 11B

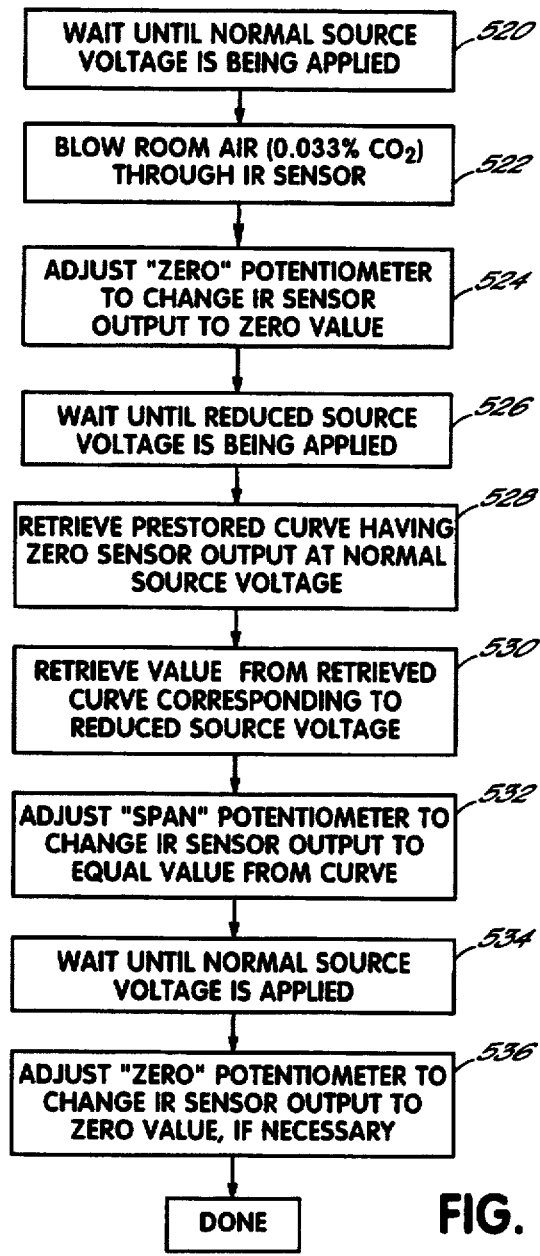
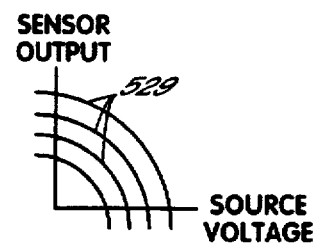
FIG. 15B
FIG. 15A
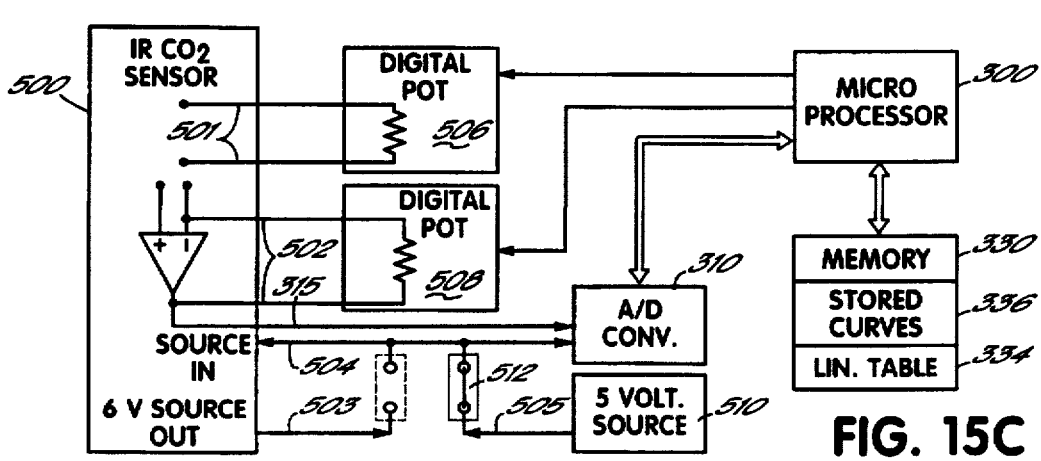
FIG. 15C

CONTROLLED ATMOSPHERE INCUBATOR

BACKGROUND OF THE INVENTION

The present invention is generally related to controlled atmosphere incubators and, more specifically, to an improved incubator used to culture biological specimens.

Growing cell cultures in a laboratory incubator requires that the atmospheric conditions, such as temperature, humidity and gas concentrations, remain constant throughout the incubator. A common manner of humidifying the culturing environment or incubator chamber is to place a stainless steel pan of water in the bottom of the incubator. The water in the pan evaporates and, since the incubator requires a gas tight seal, the humidity level inside the incubator climbs to a level above 95% relative humidity. These high levels of humidity keep the cell cultures and their associated media from drying out during incubation. This is particularly critical when the volume of media is very small and the time required to culture the cells spans, for example, several days or more.

Although it is desirable to maintain these high levels of humidity for culturing and for fast humidity recovery after the incubator door is opened, it is not desirable to have condensate form anywhere inside the incubator. Condensate creates potential places for molds, spores and other unwanted bacteria to grow. Condensate will develop on any "cold spots" when the temperature on a surface is below the dew point of the air/gas mixture inside the incubator. Generally, incubators operate at a temperature of 37° C. and at elevated humidity conditions. The dew point, for example, at 37° C. and 98% relative humidity is 36.6° C. Therefore, any surface inside the incubator at a temperature below 36.6° C. and in contact with the air/gas mixture will condense the water from the mixture in the form of small droplets. These may then develop into pools or puddles of condensate. It is desirable for this reason as well as others to maintain all interior surfaces at a constant temperature, however, there have been some practical limits that have required less than perfect conditions.

One location within the incubator where condensate tends to form is on the inner glass door to the incubator chamber. Generally, these doors are heated to prevent condensate from forming, especially after the door has been opened. For example, electric heaters are often placed in the outside, insulated door and heat generated by these heaters is conducted, convected and radiated through the air space between the outside, insulated door and the inner glass door. Because the heat must be transferred through the air gap between the two doors, heating of the inner glass door is relatively slow and inefficient. A more direct way of heating the inner glass door is disclosed in U.S. Pat. No. 4,039,775. This patent discloses silk screened conductive elements or lines on the glass such as are commonly used in automobile window defrosters. Problems with such silk screened window defrosting elements, however, include reduced visibility through the glass door. If these lines are especially close together, visibility is significantly reduced and if the lines are placed wider apart to increase visibility, sufficient heat may not be transferred to the glass door. Also, these conductive line elements tend to eliminate condensate only along the elements themselves, or if heated to the point that condensate is eliminated on the entire glass panel, then too much heat may be generated and the chamber may be overheated. Finally, these conductive lines can be damaged by abrasion and lose their conductive and heating capabilities.

Other problems associated with the inner glass door of laboratory incubators involve the gasket which seals the door to the perimeter of the chamber opening and the mountings used to connect the glass door to the incubator. Specifically, a gas tight seal is generally accomplished using a silicone "feather" gasket mounted around the opening of the chamber with the "feather" portion of the gasket providing a seal against the inner glass door in the closed position. To maintain the integrity of the seal, the conventional method of mounting the gasket to the chamber is by using a silicone adhesive/sealant. The gasket, also generally formed of silicone, is extruded in a profile that creates a groove for the adhesive. These gaskets are difficult to clean because of their relatively complex geometry. A particularly dirty gasket may be replaced in the field by peeling the gasket off the chamber, removing the excess silicone adhesive and attaching a new gasket in the same manner as the original one. This process, however, is tedious and requires significant down time. With respect to the door mountings, hinges are generally permanently mounted to the chamber by spot welds. As these hinges may not be removed, the direction that the door swings open and closed is determined by the side of the chamber having the hinges. Field reversible doors have been an even more significant problem in water jacketed incubators since these hinge mountings must generally be placed through the water jacket portion of the incubator.

An air circulation system is also a vital ingredient in creating the correct environmental conditions for the growth of cell cultures in a laboratory incubator. Air circulation is needed to maintain temperature uniformity within the chamber and also to effectively distribute and mix the various gases, such as $CO_2$ and $N_2$, used to control the pH and $O_2$ levels within the chamber. The air flow keeps the lighter gases from stratifying within the chamber and aids in the control of $CO_2$ and $O_2$ levels by providing air flow across the gas sensors. A blower is generally used in conjunction with a high efficiency particulate air or "HEPA" filter for circulating the air and removing contaminants from the air. The HEPA filters must be maintained at a temperature above the dew point of the air mixture to prevent condensation from developing inside the filter. This condensation can restrict or block the flow of air through the filter. Problems which currently exist with such air circulation systems include the requirement for an additional heat source to maintain the temperature of the HEPA filter above the dew point of the air mixture. Also, HEPA filters have generally been mounted in locations requiring the removal of side panels and other hardware associated with the incubator in order to access the filter for replacement. As the researcher or operator may be exposed to high voltage components when removing these incubator panels, a qualified service technician must be used for what should otherwise be a simple filter replacement procedure.

While more complicated humidifying devices may be used to control the relative humidity within the chamber, the simplest device and most common method involves placing a pan of water at the bottom of the chamber and allowing the chamber to become saturated through evaporation of water from the pan. Unfortunately, this simple method of humidification is not easily controlled and the resulting fully saturated condition more easily leads to the development of condensation within the chamber.

With regard to temperature control within the chamber of the incubator, a variance in the line voltage applied to electric components which generate heat will vary the heat output of the particular electric component. Inconsistent heat output of such incubator components as heaters and motors makes it difficult to accurately and uniformly control the temperature of the incubator chamber.

Laboratory incubators simulating biological conditions also generally include carbon dioxide sensors to regulate the amount of $CO_2$ within the chamber and thereby simulate a specific pH or acidity level. Two general types of $CO_2$ sensors are sensors based on a thermal conductivity detection and sensors utilizing infrared technology. With respect to thermal conductivity $CO_2$ sensors, while these sensors are generally less costly, they are also sensitive to humidity and oxygen levels and to temperature variations within the chamber. While certain compensation systems have been proposed, these systems have not entirely solved the problems with environmental sensitivities. Infrared sensors are much less sensitive to the above noted environmental conditions. However, calibration requires the use of a tank of gas having a specific percentage of $CO_2$.

In view of the above noted problems and deficiencies of incubators in general, there is a need for an incubator which provides a more accurate simulated chamber condition and which is more easily operated and maintained in the field by the end user.

SUMMARY OF THE INVENTION

The present invention is directed to an incubator which, in a first aspect, includes a double door construction wherein one door comprises an outside insulated door and the second door is an inside glass door for alternatively sealing and accessing the incubator chamber. In accordance with the present invention, the glass door is directly heated by an electrically conductive, clear coating placed on at least one surface of the door. The coating also has the characteristic of causing the glass to have low emissivity.

Specifically, a dual glass pane configuration is used having two panes of glass separated by a space and with one pane being coated and electrically heated. A pair of bus bars are disposed on opposite sides of the glass door and provide for electric conduction across the coated surface. This glass door therefore provides direct and complete heating of the glass to prevent or remove condensate on the inside surface of the glass without the disadvantages associated with indirect heating methods or typical silk screened conductive lines.

The glass door is sealed by a unique gasket which may be removed for cleaning and sterilization and replaced in a simple operation. Specifically, the gasket includes a mounting portion and an outwardly extending feather portion which seals against the inside glass surface. The mounting portion simply presses onto the perimeter or edge of the chamber opening with a friction fit. The feather or sealing portion of the gasket extends outwardly in a manner and direction which prevents buckling of the feather portion when mounted around the curved corners of the door opening.

In accordance with a further aspect of the invention, the glass door is uniquely mounted onto the front water jacket portion of the incubator to allow the door to be easily reversed in the field from left to right swinging or vice versa.

In accordance with another aspect of the invention, the air flow pattern within the incubator is created by a blower assembly mounted within the incubator chamber in an easily accessible manner. Air is pulled into a blower near the top of the chamber and exhausted through duct work that runs across the top of the chamber, down a plenum located behind a shelf support panel in the chamber and across the bottom of the chamber until the air disperses and is pulled up vertically through perforated shelves located inside the chamber. In accordance with the invention, a HEPA filter is mounted directly to the blower and is located internally to the chamber. Therefore, the blower assembly does not require an additional heat source to maintain its temperature above the dew point of the air mixture within the chamber. The HEPA filter is also easily removed and replaced by a researcher or other user from within the chamber and does not require the removal of side panels or other hardware which might involve exposure to high voltage wiring and/or components.

The invention further contemplates a control volume approach to regulating the humidity level within the chamber. Specifically, relatively low humidity ambient air is drawn into the inlet of the blower through a filter and, at the same time, air exits the chamber through a filtered outlet. This air exchange prevents complete saturation of the incubator chamber and therefore assists in preventing the formation of condensation inside the incubator. HEPA filters are preferably used to filter both the incoming ambient air as well as the air exiting the chamber. This minimizes the potential for introducing contamination into the incubator and allowing escape of contamination from the incubator. As this air exchange system is formed as part of the internal air circulation system in this unique manner, no additional components or electronics are necessary for controlling the relative humidity within the chamber.

The motor for operating the blower is mounted directly above and against the top of the incubator chamber. The control of the present invention operates to maintain constant power, and therefore constant heat generation, from the motor during voltage and frequency variations. Specifically, the invention features a method and apparatus for controlling application of a line voltage to an electric motor in the chamber, to reduce variations in heat produced by the motor that might be caused by line voltage variations. In accordance with this aspect, the line voltage and/or frequency is measured and, based on performance characteristics of the motor, the line voltage is applied to the motor in a pattern which will result in a predetermined net root-mean-square voltage across the motor, and consequently a predetermined amount of heat.

In particular embodiments, the line voltage is an AC line voltage, applied to the motor through a triac. The triac is activated a variable delay time after a zero crossing of the line voltage (and automatically deactivates when the motor current reaches zero). The appropriate delay time for a given RMS line voltage is determined by applying various line voltages and frequencies, and various delay times, to determine a delay time for each line voltage and frequency which results in a predetermined RMS voltage across the motor's terminals. This delay time is then stored in the table for later retrieval and use in controlling the motor.

In accordance with another aspect, the operation of a heater under the control of a closed-loop temperature control system is improved by reducing variation in the heater's heat output caused by line voltage variation. The closed-loop temperature control is calibrated for operation at a predetermined line voltage, such as 90 Volts RMS, and in operation generates a heater power fraction indicating the fraction of full heater power to be applied to the chamber. The control circuit determines a ratio of the root-mean-square amplitude of the measured line voltage to $(90)^2$. Then, a revised heater power fraction is obtained by dividing the heater power fraction demanded by the closed-loop temperature control system by the computed ratio. The heater then generates the revised heater power fraction of its maximum heat output. As a result, the closed-loop temperature control system will obtain a consistent heat output from the heater independent of variations in line voltage.

In preferred embodiments, the line voltage is an AC line voltage which is alternately applied, and not applied, to the heater, such that power is applied to the heater for a fraction of time equal to the revised heater power fraction.

In accordance with another aspect, a gas sensor such as a thermal conductivity carbon dioxide sensor is calibrated to compensate for sensitivities to oxygen and/or humidity, by measuring the temperature and humidity and/or oxygen in the vicinity of the gas sensor, and then determining a humidity and/or oxygen variation between said the current humidity/oxygen level and the humidity/oxygen level extant when the gas sensor was calibrated. Next, the incubator temperature is used to determine an amount of humidity and/or oxygen variation which would cause a one percent apparent change in gas concentration indicated by the gas sensor. Then the humidity and/or oxygen variation is divided by the amount of humidity/oxygen variation which would cause a one percent apparent change in gas concentration, and the resulting value is added to the gas concentration indicated by the gas sensor, thus compensating the gas sensor reading for variations in humidity and/or oxygen.

In preferred embodiments, the humidity sensor measures a relative humidity level, and this relative humidity level is converted to grains based on the measured temperature, so that the grains may be used to compute the apparent change in gas concentration caused by humidity variation.

In another aspect, the invention features a circuit for detecting whether an incubator door is open. The door has a conductive frame attached thereto which is electrically isolated from the grounded frame of the chamber. When the door is closed, the conductive door frame contacts the chamber frame and the door frame is thereby grounded. However, when the door is open, no such contact is made, so that a pull-up circuit electrically connected to the door frame pulls the door frame up to a logic "high" voltage (e.g., 5 volts) which can be detected by logic circuitry in the controller and used to indicate that the door is open.

In preferred embodiments, the logic circuitry includes electrostatic isolation circuitry which protects the controller from electrostatic discharge in the door conductor.

An optional infrared based carbon dioxide sensing element or detector is also contemplated by the present invention. In accordance with the invention, a unique calibration method eliminates the need for a separate supply of calibrating gas. This calibration procedure takes advantage of uniform ambient air conditions wherein $CO_2$ represents 0.033% of the volume of ambient air. Specifically, a predetermined concentration of gas is applied to the sensor, and then the sensor output is measured when the normal power is applied to the light source, and when a reduced power level is applied to the light source. These two measurement points are then curve-matched to a known, predetermined curve of source power vs. sensor output for the sensor, to produce an offset and gain factor to be applied to further sensor readings.

Further objects and advantages of the present invention will become more readily apparent to those of ordinary skill upon review of the following detailed description taken in conjunction with the accompanying drawings.

BRIEF DESCRIPTION OF THE DRAWINGS

FIG. 10A is a circuit diagram of the RMS to DC Converter circuit of FIG. 9;

FIG. 10B is a circuit diagram of the Zero Crossing Detector of FIG. 9;

FIG. 10C is a circuit diagram of the Fan Motor Control of FIG. 9;

FIG. 11A is a flow chart of operations taken by the microprocessor of FIG. 9 to compensate the motor power consumption for line voltage variations;

FIG. 11B is a timing diagram useful in understanding the circuit of FIG. 10C and operations described in FIG. 11A;

FIG. 15A is a flow chart of operations taken by the microprocessor of FIG. 9 to calibrate an infrared $CO_2$ sensor;

FIG. 15B illustrates stored curves used by the microprocessor of FIG. 9 to calibrate an infrared $CO_2$ sensor; and FIG. 15C is a block diagram of an infrared $CO_2$ sensor and the circuitry used by a microprocessor 300 to calibrate this sensor.

DETAILED DESCRIPTION OF THE PREFERRED EMBODIMENT

Figure 1:
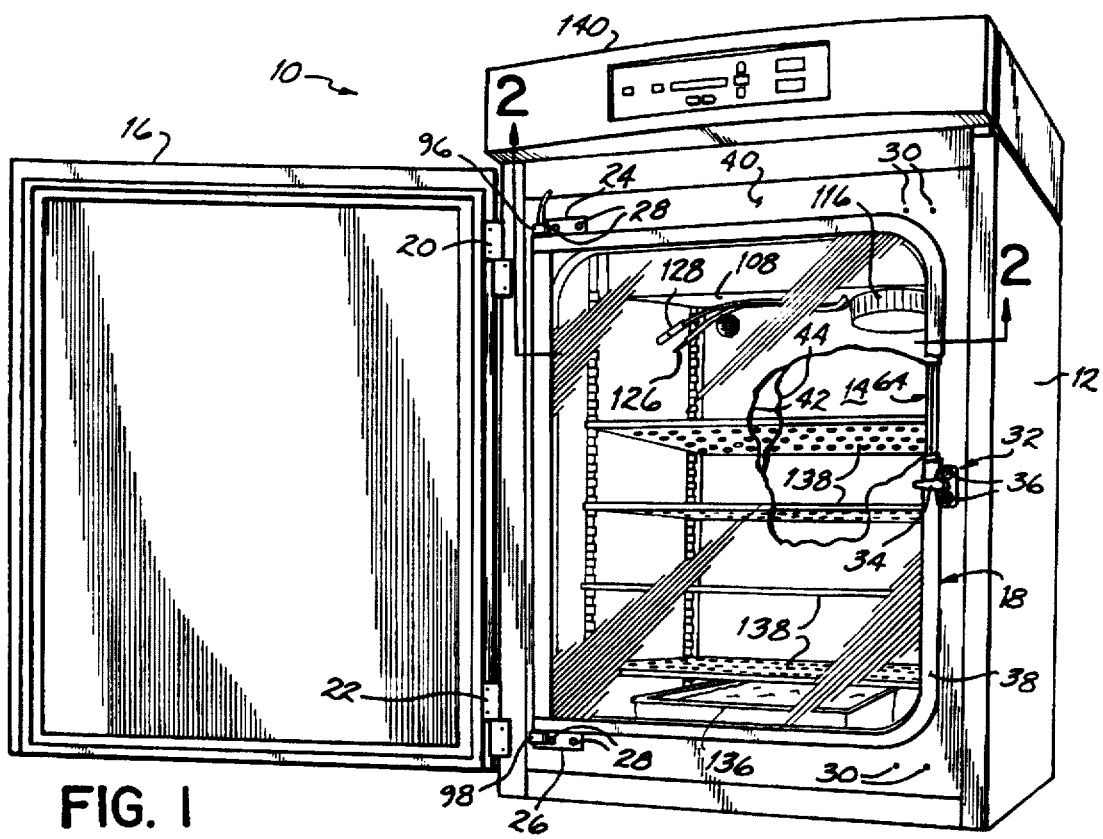
FIG. 1 is a perspective view of an incubator constructed in accordance with the present invention.

FIG. 1 illustrates an incubator 10 constructed in accordance with the present invention and generally including an insulated, and preferably water-jacketed, cabinet 12 with an interior controlled atmosphere chamber 14. Chamber 14 is accessed through a pair of doors which include an outer insulated door 16 and an inner heated glass door 18. Insulated door 16 is attached to cabinet 12 by a pair of hinges 20, 22 which may be alternatively attached to the left or right side of cabinet 12 depending on which direction it is desired to swing insulated door 16. Likewise, inner glass door 18 includes hinges 24, 26 secured by fasteners 28 to front panel 40 of cabinet 12. Fasteners 28 and their associated receiving elements will be described in more detail below, however, in general these fasteners 28 and receiving elements 30 allow fastening of door 18 to front panel 40 in either a left or right swinging manner. Fastener receiving elements 30 are installed permanently on both the left and the right side of front panel 40 and are sealed into the water jacket portion of cabinet 12. Door 18 further includes a latch assembly 32 having a twist latch 34 fastened to front panel 40 by fasteners 36. Latch 34 bears against frame 38 of door 18 when in the latched position to seal door 18 against front panel 40 as will be described below.

Figure 2:
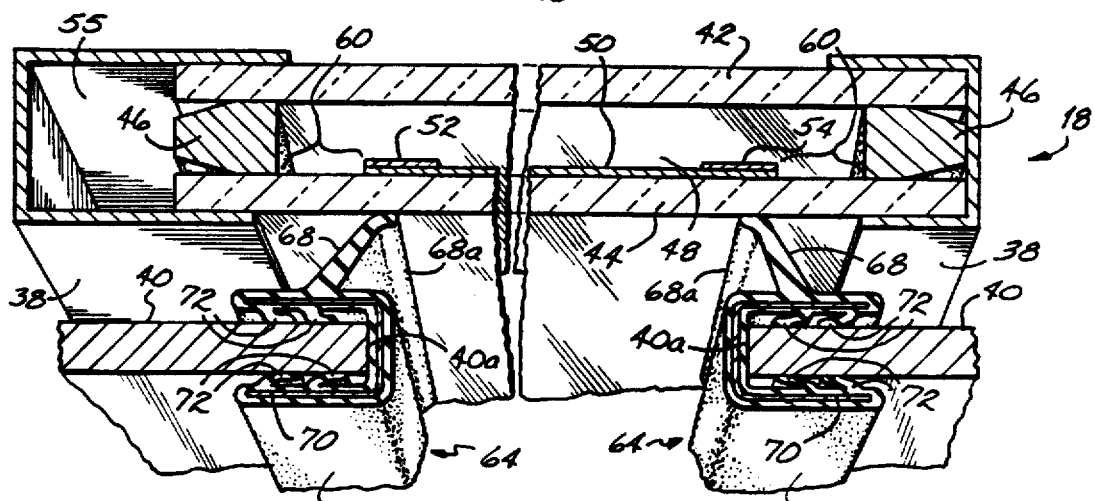
FIG. 2 is a fragmented cross sectional view of the inner glass door in perspective and taken generally along line 2—2 of FIG. 1.

FIG. 2 illustrates the specific construction of inner glass door 18 as well as the manner of forming a gas-tight seal between door 18 and front panel 40 of cabinet 12. Inner glass door 18 includes two glass panes 42, 44 separated by an aluminum spacer 46 to create an intermediate air gap 48. Inner pane 44 includes a low emissivity coating 50 on the inner surface thereof between a pair of bus bars 52, 54 silk screened over edge portions of coating 50. Coating 50 preferably comprises a conventional clear, tin oxide coating. Bus bars 52, 54 are electrically connected to a control, to be described below, to apply current therebetween and through coating 50. A channel 55 is created within frame 38 on the hinge side of glass door 18 to route wiring from bus bars 52, 54 to the control to be described. Coating 50 is heated and prevents the formation of condensation. If condensation has already formed on the chamber side of pane 44, such condensation is evaporated by the heat generated by coating 50. The entire perimeter 60 of inner pane 44 is void of coating 50 so that conduction does not take place through the aluminum spacer 46 in a manner which bypasses coating 50.

FIG. 2 also illustrates the unique gasket 64 of the present invention as it seals against inner pane 44. Gasket 64 specifically includes a mounting portion 66 which is trough-shaped or U-shaped in cross section so that it may easily fit over the edge 40a of front panel 40 which defines the opening to chamber 14 (FIG. 1). A sealing portion or feather 68 extends outwardly from mounting portion 66 and maintains sealing engagement with inner glass pane 44 when door 18 is in the closed position. Mounting portion 66 and feather 68 are preferably extruded together from silicone and, extruded within mounting in portion 66 is a wire 70 which lends structural rigidity to gasket 64. The U-shaped mounting portion 66 further includes locking elements 72 which engage on opposite sides of panel 40 to retain gasket 64 in position about the opening to chamber 14.

Figure 2A:
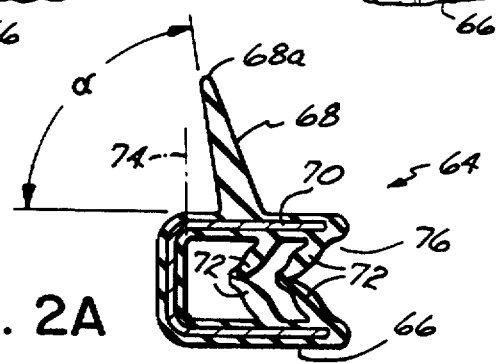
FIG. 2A is a cross sectional view of the gasket shown in FIG. 2 but removed from the incubator.

Referring now to FIG. 2A, gasket 64 is uniquely constructed such that feather 68 will not buckle or become rippled when gasket 64 is bent around the relatively small radius corners of the opening to chamber 14 (FIG. 1). The angle α and the placement of feather 68 with respect to the approximate bending plane 74 of gasket 64 are chosen such that tip 68a of feather 68 is positioned inside of the approximate bending plane 74. That is, tip or edge portion 68a lies on the side of bending plane 74 which is closer to the open end 76 of the U-shaped mounting portion 66. In the preferred embodiment, angle α is approximately 80°.

Figure 3:
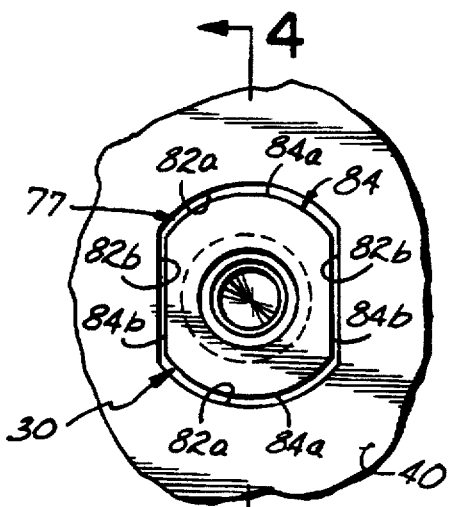
FIG. 3 is a front elevational view of a fastener receiving element used to mount the inner glass door to the incubator cabinet.
Figure 4:
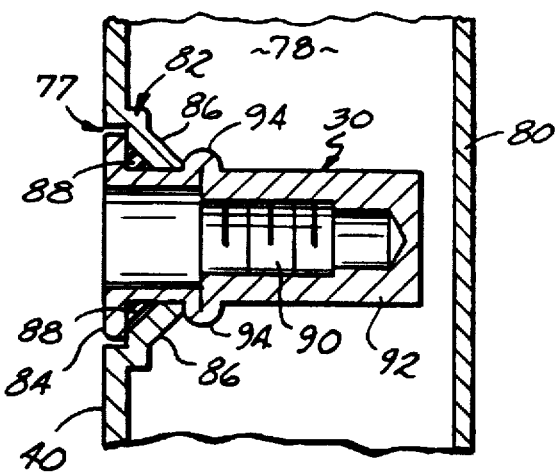
FIG. 4 is a cross sectional view of the fastener receiving element taken along line 4—4 of FIG. 3.

Referring now to FIGS. 3 and 4, a fastener receiving element 30 for fastening door 16 to cabinet 12 is shown in greater detail. As shown best in FIG. 4, these fastener receiving elements 30 are fastened onto front panel 40 and extend through an opening 77 in front panel 40 into a water jacket 78. Water jacket 78 is defined between front panel 40 and a second inner panel 80. Water jacket 78 preferably extends along the top, bottom, rear and two sides of cabinet 12. As also shown in FIG. 4, opening 77 in front panel 40 is deformed such that a stepped down portion 82 is formed for receiving a head or flange 84 of the fastener receiving element 30. As shown in FIG. 3, both the stepped down portion 82 and the head or flange 84 of receiving element 30 are formed with the same, noncircular shape such that head 84 may not rotate with respect to front panel 40 when a fastener 28 (FIG. 1) is threaded into receiving element 30. In the preferred embodiment, both the stepped down portion 82 and head 84 have a "race track" shape with two parallel curved sides 82a, 84a and two parallel straight sides 82b, 84b.

Referring back to FIG. 4, opening 77 in panel 40 which accepts receiving element 30 further includes an angled portion 86 which acts as a sealing surface with an O-ring 88 situated between flange or head 84 and angled portion 86. Finally, fastener receiving element 30 includes internal threads 90 which accept both a tool for crimping the receiving element 30 into place on front panel 40 and accepting conventional threaded fasteners 28 for removably securing glass door 18 to front panel 40 (FIG. 1). With regard to the crimping process for attaching receiving element 30 to front panel 40, it will be appreciated from FIG. 4 that a tool, such as a pneumatic tool, is used to pull the inner threaded portion 92 of element 30 toward head or flange portion 84 to create an outwardly deformed area 94 which bears against angled portion 86. This tightly traps O-ring 88 between flange or head portion 84 and angle portion 86. In this way, a water tight seal is created which prevents leakage from water jacket 78 at the site of each fastener receiving element 30.

Referring now briefly to FIG. 1, it will be appreciated that the placement of fastener receiving elements 30 in upper and lower positions on both the right and left hand sides of front panel 40 allows glass door 18 to be easily switched from left to right swinging by simply removing fasteners 28 from, for example, the left side, flipping door 18 over and fastening hinges 24 and 26 to the right side fastener receiving elements 30 using the same threaded fasteners 28. As also shown in FIG. 1, the side of door 18 which includes hinges 24, 26 also includes identical electrical connectors 96, 98 on upper and lower edges thereof for making the appropriate electrical connection to bus bars 52, 54 (FIG. 2) at an upper end of door 18 whether door 18 is swinging from the left or the right. Both electrical connectors 96, 98 are connected to wiring (not shown) contained in channel 55 (FIG. 2). This makes the electrical connection with electrical control hardware components to be described below easier as these components are contained in the top of incubator 10.

Figure 5:
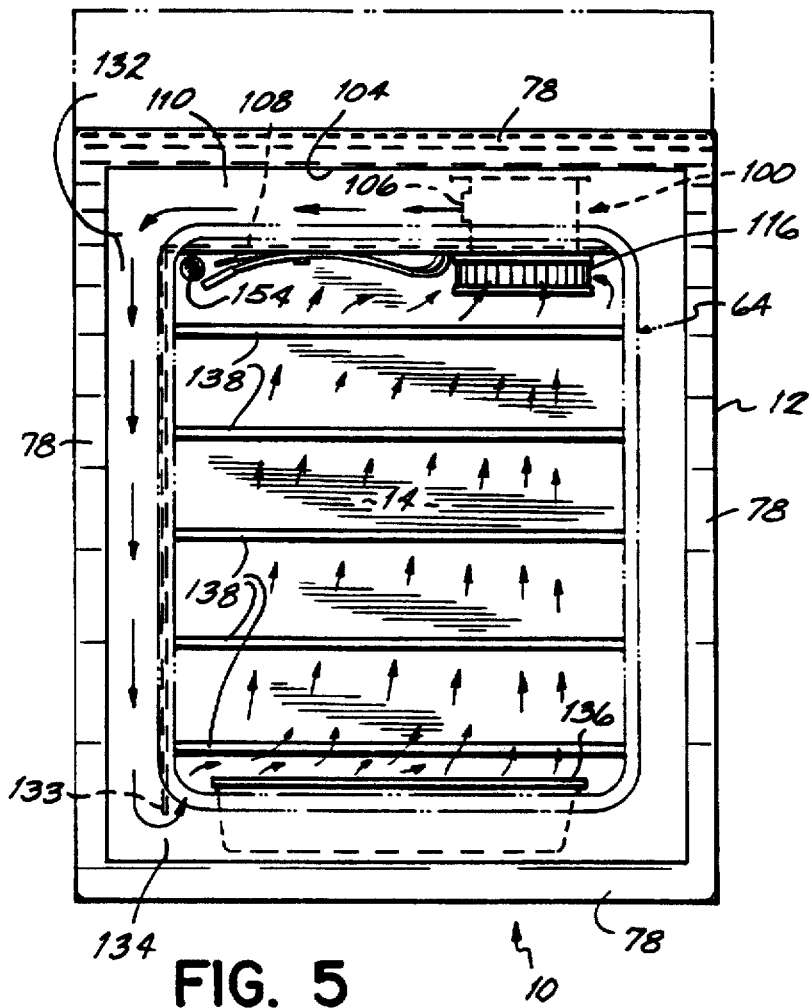
FIG. 5 is a diagrammatic front view showing the air flow pattern and blower assembly within the incubator chamber.
Figure 6:
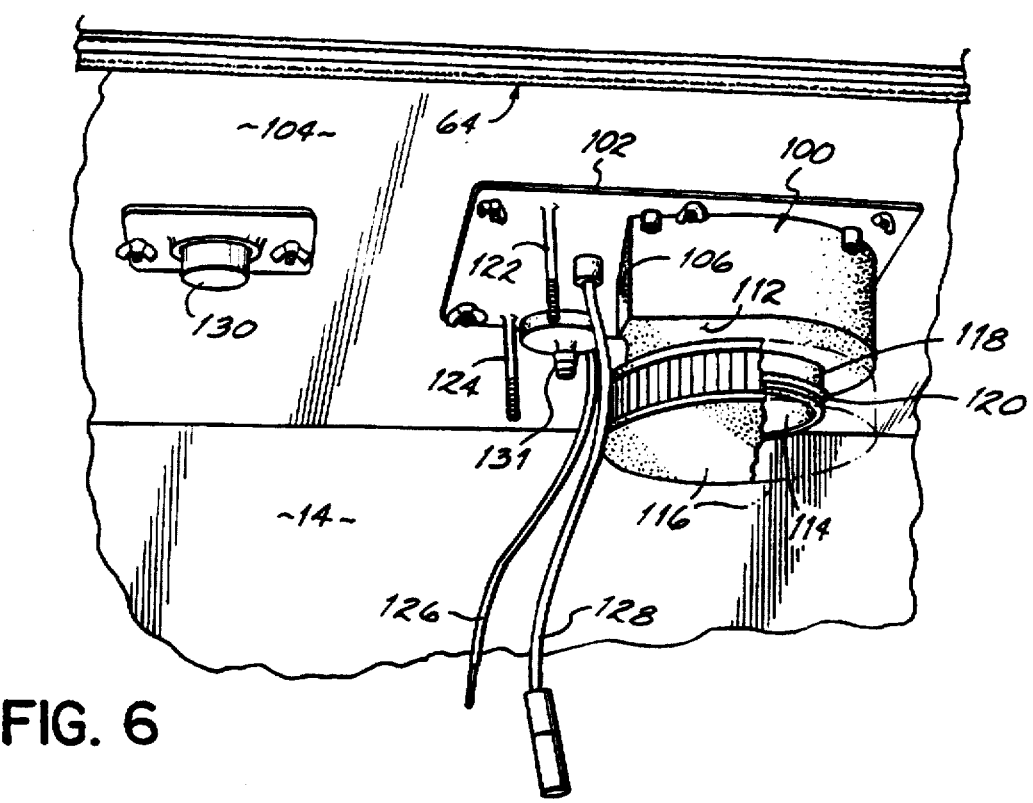
FIG. 6 is a fragmented perspective view showing the blower assembly and $CO_2$ sensor at the top of the incubator chamber with an upper plenum-defining plate removed for clarity.

Referring now to FIGS. 5 and 6, the unique HEPA air circulation system of the invention includes a blower assembly 100 which is mounted to a plate 102 (FIG. 6) at an upper end of chamber 14. Mounting plate 102 is fastened to an upper panel 104 of chamber 14. As appreciated from FIG. 5, an outlet 106 of blower assembly 100 is situated between panel 104 and a panel 108. An upper plenum 110 is defined between panels 104, 108 and extends across the top of chamber 14. In FIG. 6, panel 108 has been removed for clarity but, in practice, sits against surface 112 of blower assembly 100 between outlet 106 and an inlet 114 to which is attached a HEPA filter 116. HEPA filter 116 is mounted to a cylindrical extension 118 defining inlet 114 of blower assembly 100. Extension 118 includes an O-ring seal 120 for sealing the removable connection made between HEPA filter 116 and extension 118. As appreciated from FIG. 5, HEPA filter 116 may be easily removed and replaced from within chamber 14. Plate 108 is removably fastened in the upper portion of chamber 14 to a pair of threaded elements 122, 124 extending downwardly from mounting plate 102. Thus, plate 108 may also be easily removed to allow maintenance and replacement of the entire blower assembly 100 from within chamber 14. Also extending from plate 102 is a temperature probe 126 and a humidity sensor 128. Probe 126 and humidity sensor 128 are connected to further control hardware located at the top of incubator 10 and function in a manner to be described. Also contained within upper plenum 110 is a $CO_2$ sensor 130 which may be of a thermal conductivity or infrared variety as will also be described below. The $CO_2$ sensor 130 is therefore mounted in the path of filtered air exiting blower assembly 100 and may also be easily accessed from within chamber 14 after removing plate 108. A HEPA filtered sample port 131 is also mounted to plate 102 for drawing test samples of air from chamber 14.

As shown in FIG. 5, chamber 14 further includes a side plenum 132 which connects with upper plenum 110 and which has a lower opening 134. Side plenum 132 is disposed behind a shelf support panel 133 within chamber 14. Air is drawn into the HEPA filtered inlet 114 (FIG. 6) of blower assembly 100, exits across upper plenum 110 and past $CO_2$ sensor 130. The filtered air then moves downwardly through side plenum 132, through opening 134 and across a conventional pan 136 which holds water for humidifying chamber 14. As shown in FIG. 1, shelves 138 mounted within chamber 14 are perforated to allow air circulation upwardly and finally back through HEPA filter 116.

Figure 7:
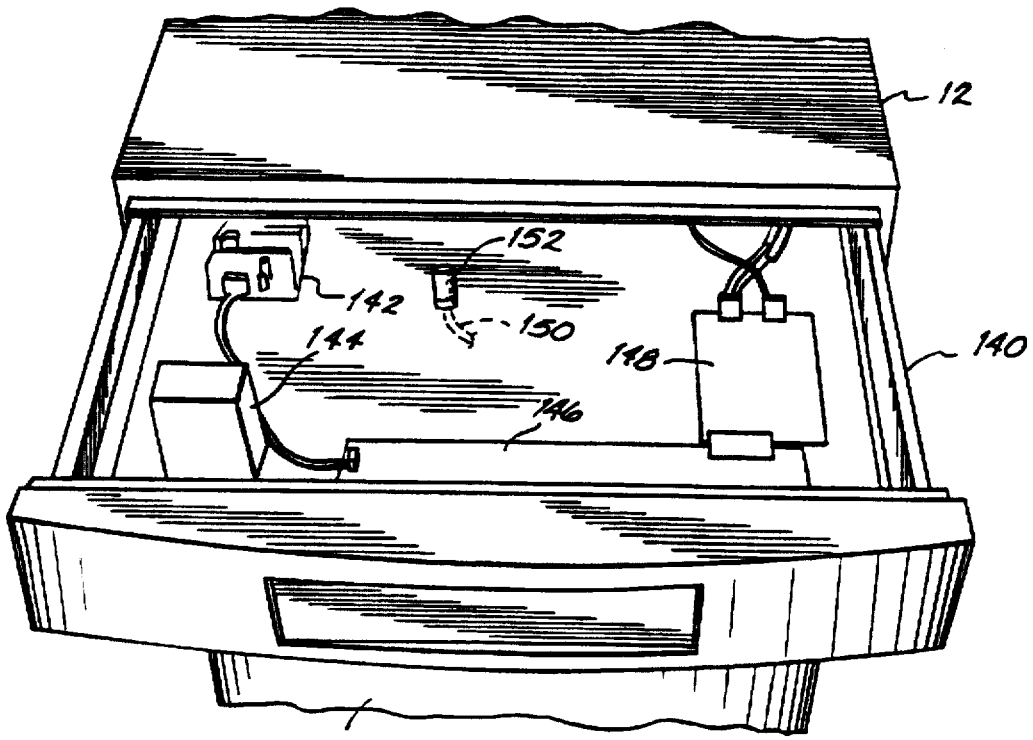
FIG. 7 is a perspective view of the incubator cabinet with the upper drawer opened to show various control components therein.
Figure 8:
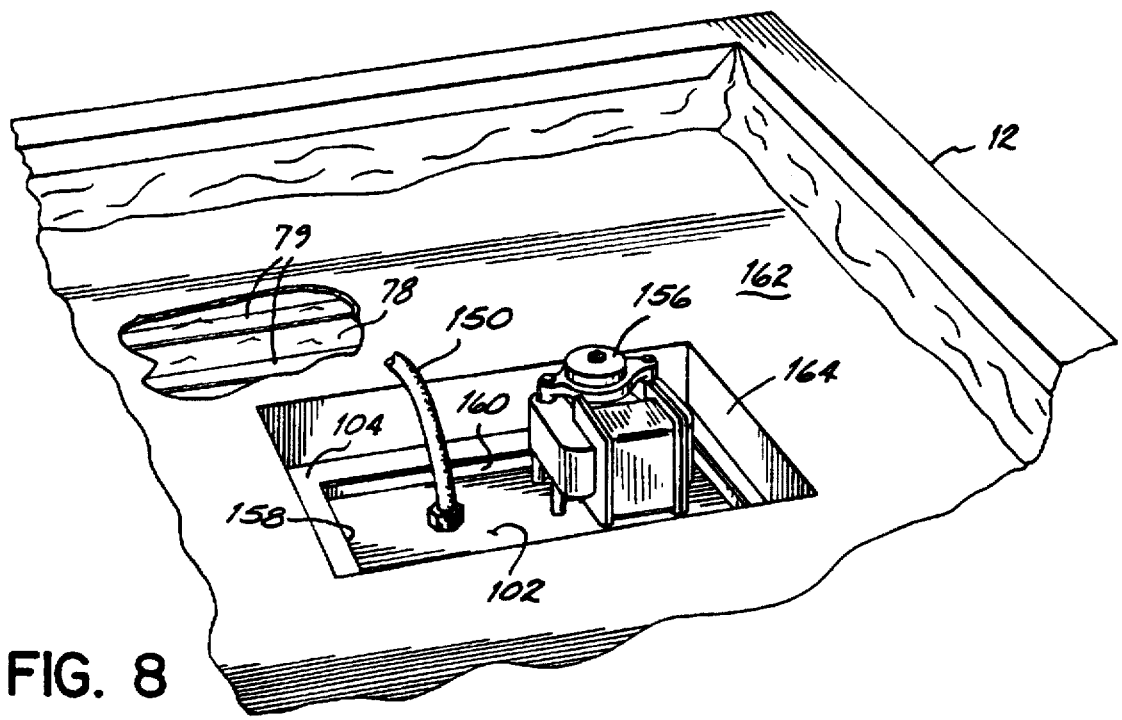
FIG. 8 is a perspective view of the interior top of the incubator cabinet which holds the motor for operating the blower assembly.

Referring now to FIG. 7, the upper end of cabinet 12 includes a drawer 140 for conveniently holding the various hardware components 142, 144, 146, 148 as well as others, not shown, which are necessary in the implementation of the control to be described below. Drawer 140 therefore allows easy maintenance and replacement of these components without necessitating the removal of panels as is conventional. As further shown in FIG. 7, an air inlet line 150 extends into drawer 140 and includes a HEPA filter 152 attached on the end. This air inlet line 150 is used to draw in relatively dry or low humidity ambient air into chamber 14 by being connected to the inlet of blower assembly 100. As shown in FIG. 8, line 150 extends through mounting plate 102 and is suitably attached to communicate with the inlet of blower assembly 100 (FIG. 5). Filter 152 controls the amount of ambient air being drawn in and is preferably a HEPA filter which has a flow rate of ¹⁄₁₀ c.f.m. Other manners of regulating the flow rate to ¹⁄₁₀ c.f.m. are also possible. As shown in FIG. 5, a HEPA-filtered outlet 154 is disposed in the back wall of chamber 14 and also leads to the ambient environment. The same HEPA filter as filter 152 is preferably disposed within outlet 154. The constant exchange of air, i.e., by ambient air being drawn in through inlet 150 at about ¹⁄₁₀ c.f.m. and chamber air leaving through outlet 154 at the same rate, provides a simple control volume approach to help insure that chamber 14 does not reach a saturated state. This helps prevent the formation of condensation within chamber 14.

Referring back to FIG. 8, a motor 156 is secured to mounting plate 102 and extends through an opening 158 in upper panel 104. A gasket 160 is disposed between mounting plate 102 and upper panel 104. This arrangement allows motor 156 to be mounted outside of incubator 14 but directly adjacent thereto so that it may be easily connected to blower assembly 100 (see FIGS. 5 and 6). A top section 162 of water jacket 78 is formed with a portion 164 cut out to allow the mounting of motor 156 directly against mounting plate 102 and to also allow the filtered ambient air inlet 150 as well as other control components to extend into incubator 14 from, for example, drawer 140 (FIG. 7). As also shown in FIG. 8, water jacket 78 is preferably thermally connected with electric heating elements 79 for directly heating the water therein and indirectly heating incubator 14 in a uniform manner (FIG. 1). Although elements 79 are shown in the top of water jacket 78, it will be understood that such elements may also be placed, or alternatively be attached outside water jacket 78 in the same or other locations.

Figure 9:
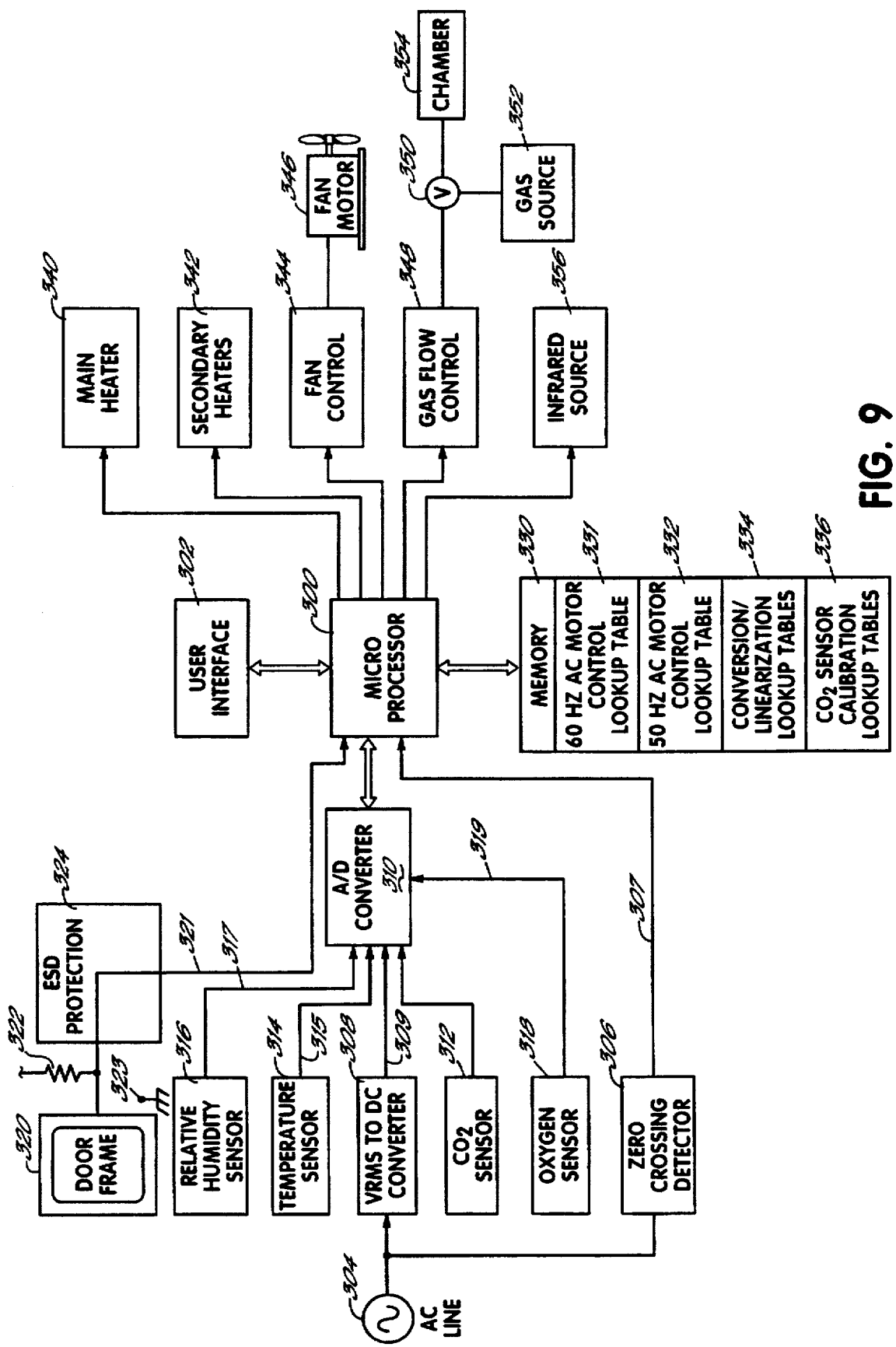
FIG. 9 is a block diagram of the control and sensor circuitry used for the chamber's environmental control system.

Referring now to FIG. 9, the electrical control system for the incubator's environmental control is centered around a microprocessor 300 which receives data from sensors and a number of other sources, and controls the heater, fan and gas flow into the incubator.

Microprocessor 300 produces displays on a character display on the front of the unit, and is able to receive commands from a user through keystrokes on keys located adjacent to the display. This display and the keys next to it form a user interface 302 through which microprocessor 300 can be controlled by a user. Using this user interface, the user may set the incubator temperature, set the carbon dioxide or other gas levels in the incubator, and enable calibration of the various sensors used by the incubator to control these environmental parameters.

As is discussed in further detail below, the performance of the heater and of the fan motor are subject to variation upon variation of the AC line voltage or AC line frequency produced by the wall outlet from which the circuitry is drawing power. To compensate for these possible variations, the voltage and the frequency of the AC power are detected, and the voltage is used to compensate the heater, while voltage and frequency are used to compensate performance of the fan motor. The AC line voltage is represented in FIG. 9 by voltage source 304. A zero crossing detector 306 is used to detect the frequency of the AC line voltage from source 304. At the same time, a RMS to DC converter 308 is used to detect the amplitude of the AC line voltage. Zero crossing detector 306 produces a logic signal pulse on line 307 corresponding to each zero crossing of the AC line voltage 304. These logic pulses are used by microprocessor 300 to determine the frequency of the AC line voltage. RMS to DC converter 308 determines the amplitude of the AC line voltage and produces an analog output voltage on line 309 proportional thereto. This analog output voltage is converted by an A/D converter 310 to a digital value which may be used by microprocessor 300. As is elaborated in further detail below, the voltage amplitude of the AC line can then be used by microprocessor 300 to calibrate the operation of incubator heaters and used in conjunction with the frequency to control the fan motor.

Microprocessor 300, as noted above, controls the temperature and carbon dioxide level within the incubator to desired levels requested by the user through user interface 302. To perform this control, microprocessor 300 obtains a reading of the carbon dioxide level in the incubator from a carbon dioxide sensor 312, and obtains a reading on the temperature in the incubator from a temperature sensor 314.

Temperature sensor 314 is a temperature sensitive electrical device such as a thermistor coupled to analog circuitry which produces an analog voltage on line 315 proportional to the temperature in the incubator. This analog voltage is converted by A/D converter 310 to a digital value which may be read by microprocessor 300.

Carbon dioxide sensor 312 may be a thermal conductivity carbon dioxide sensor or an infrared carbon dioxide sensor. Thermal conductivity carbon dioxide sensors measure thermal conductance between two points and from this produce an analog signal which is representative of the carbon dioxide content in the region between those two points. This kind of carbon dioxide sensor is relatively inexpensive, however, it is sensitive to humidity and oxygen level variation and thus is susceptible to errors if such variations occur in the incubator. Infrared carbon dioxide sensors are not sensitive to humidity and oxygen levels, however, such sensors are expensive (due to various complex supporting circuitry) and may be complex to calibrate using known procedures. Each of these drawbacks of carbon dioxide sensors is alleviated through principles of the present invention, as discussed below.

When a thermal conductivity carbon dioxide sensor is used for sensor 312, in accordance with principles of the present invention, sensitivities to humidity and oxygen concentration are compensated through the use of humidity and oxygen sensors 316 and 318.

Humidity sensor 316 is a relative humidity sensor which produces a signal related to relative humidity within the incubator. This signal is impressed on line 317 leading to A/D converter 310, and is converted to a digital signal read by microprocessor 300 to determine the relative humidity within the incubator.

Figure 13B:
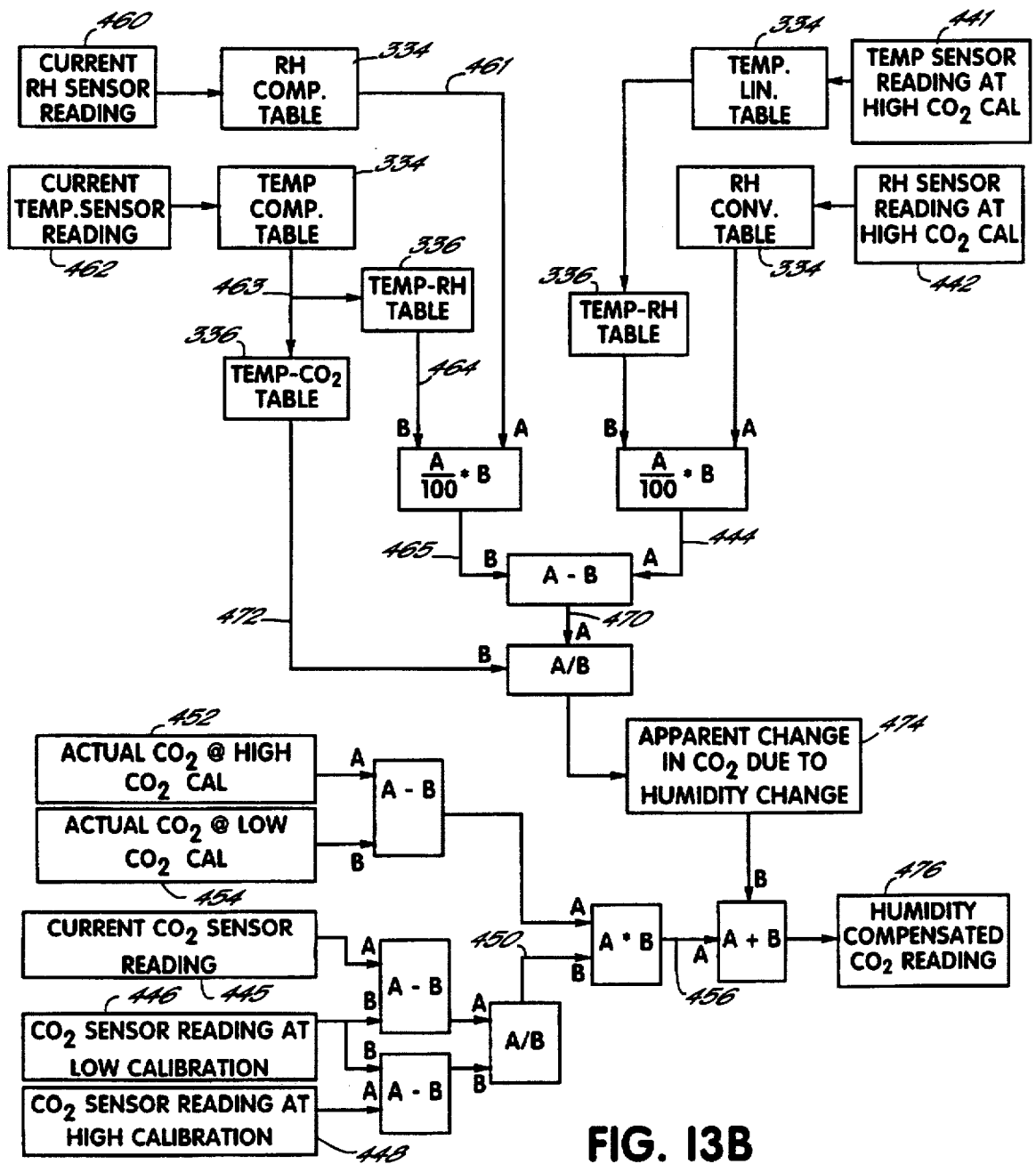
FIG. 13B is a mathematical operation diagram illustrating the method of compensation described in FIG. 13A.

Oxygen sensor 318 produces a millivolt level signal linearly related to the oxygen concentration within the incubator. This analog signal appears on line 319 and is converted by A/D converter 310 for use by microprocessor 300. The output signal from oxygen sensor 318 is converted to a signal representative of oxygen content by applying a high oxygen level to oxygen sensor 318, and storing the sensor output level for this extreme of oxygen concentration. The sensor output at 0% oxygen is approximately 0 volts. Further oxygen signal levels may be measured against those extremes using linear interpolation to determine a corresponding oxygen level. An operation of this kind is discussed below in FIG. 13A and 13B in connection with linearization of readings from carbon dioxide sensor 312.

A final input signal to microprocessor 300 is obtained from a door open detection circuit on line 321. The frame of the incubator door 320 is a conductor of a switch circuit, and is isolated from the frame of the incubator whenever the door is open. When the door is closed, door frame 320 electrically contacts the incubator and thereby becomes grounded through a connection 323. A pullup voltage (for example, 5 volts) is applied through a pullup resister 322 to cause door frame 320 to elevate to the pullup voltage whenever the door is open and not contacting the incubator frame. However, when door frame 320 is contacting the incubator frame, door frame 320 is at a ground potential. Thus, the voltage of door frame 320 is a logic-level signal indicative of whether door frame 320 is in contact with the incubator frame or not, and thus indicates whether the door is open. This signal is fed directly to the microprocessor 300 on line 321. Circuit 324 includes electrostatic discharge protection circuitry coupled to line 321 to protect microprocessor 300 and other electrostatic sensitive circuitry in the incubator controller from possible electrostatic discharge which may occur into door frame 320.

Microprocessor 300 evaluates and processes all of the signals described above from various input sources in accordance with procedures discussed in the following figures. In these procedures, microprocessor 300 makes use of a number of lookup tables found in a memory 330. These tables include motor control lookup tables 331 and 332. Table 331 is used for controlling fan motor when 60 Hz AC power is being applied, and table 332 is used to control the fan motor when 50 Hz AC power is being applied.

Also stored in memory 330 are conversion and linearization lookup tables 334 which are used to convert and/or linearize signals obtained from various climate control sensors discussed above. Specifically, for example, temperature sensor 314 produces an analog signal which is roughly linear with temperature, but includes some variations from a linear curve. Microprocessor 300 converts temperature readings obtained through A/D converter 310 by using the temperature reading obtained through A/D converter 310 as an address into a lookup table 334, to retrieve a corresponding compensated linearized temperature reading. The lookup table 334 used for temperature sensor linearization is generated from published formulas for thermistor characteristics obtained from the manufacturer of the thermistor used as temperature sensor 314, and is able to compensate temperature sensor readings to an accuracy from about ±0.2° C.

Another lookup table 334 is used to convert digitized signals from humidity sensor 316 into corresponding relative humidity values. As noted above, humidity sensor 316 produces an analog signal related to relative humidity. Once digitized, this relative humidity signal is converted to a digital number indicated 0–100% relative humidity using a second lookup table 334.

A third lookup table 334 is used to linearize signals from carbon dioxide sensor 312. The infrared carbon dioxide sensor output signal is not linear with variations in carbon dioxide concentration. The lookup table compensates for these nonlinearities. The thermal conductivity $CO_2$ sensor output is linear with variations in $CO_2$ concentration.

The last set of tables 336 stored in memory 330 is used, in a manner elaborated below, to calibrate the output of a thermal conductivity carbon dioxide sensor 312, by compensating for sensitivities of this sensor to humidity variations. The details of the use of these tables will be elaborated below.

Microprocessor 300 is also connected to various climate control elements in the incubator. These include a main heater 340 which is connected to the AC line voltage to produce heat to warm a water jacket surrounding the incubator, and secondary heaters 342 which are used to heat the inner door and front of the chamber. In addition, a fan control 344 is used to control a fan motor 346 to circulate air within the incubator. A gas flow control circuit 348 is used to control a valve 350 to permit gas (such as carbon dioxide) from a gas source 352 to enter incubator 354. Finally, if an infrared carbon dioxide sensor 312 is in use, microprocessor 300 controls a source 356 of infrared light used to stimulate the infrared carbon dioxide sensor 312. (See FIG. 15C, below.) Referring now to FIG. 10A, the RMS to DC converter 308 is an analog circuit for detecting the amplitude of the voltage of the AC power line 304. The circuit includes a transformer 360 for stepping the AC line voltage down to a manageable level, followed by a filtering circuit 362 comprising two resistors and a capacitor, which removes high frequency noise from the AC line 304. The output of this filter feeds an RMS to DC chip 364 which produces an output on line 365 which is an analog voltage representative of the root mean square amplitude of the voltage on AC line 304. A suitable RMS to DC chip 364 can be purchased from Analog Devices of Norwood, Mass., as Part No. AD736. The analog voltage on line 365 is conditioned by an operational amplifier circuit 366 configured as a follower circuit. The resulting conditioned analog signal on line 309 is converted by A/D converter 310 to a digital signal indicative of the AC line amplitude.

Referring now to FIG. 10B, the zero crossing detector 306 is an analog circuit connected to AC line 304, which detects reversals in polarity of AC line 304. In this circuit AC line 304 is connected through resisters 370 to a pair of light emitting diodes, and an associated optically coupled transistor. The diodes and optically coupled transistor are enclosed within a single optical isolation chip 372. Whenever AC line 304 is at a substantial positive or negative voltage, one of the diodes in chip 379 is turned "on", and as a result the transistor in chip 372 is turned on, drawing node 373 near to a ground potential. However, when AC line 304 nears zero, current does not flow through either of the light emitting diodes in chip 372, and these diodes turn off. This causes the transistor in chip 372 to turn off, after which node 373 raises to a pullup voltage. Thus, a positive pulse is produced on node 373 during each zero-crossing of the AC line. An invertor 374 is connected to node 373, so that circuit 306 produces a signal on line 307 that has a logic "0" pulse occurring at each zero crossing of the AC line, and otherwise has a logic "1" value. (See FIG. 11B.)

Now referring to FIG. 10C, the fan motor control circuit 344 is a similar analog circuit driven by a motor control signal. This motor control signal drives the base of a transistor 376, the collector of which is connected to an optical isolation chip 378. Optical isolation chip 378 optically couples a diode to a diac 379, such that when current flows through transistor 376, diac 379 is turned "on" and creates a short circuit between its terminals. Diac 379 is, in turn, coupled across the control and one signal terminal of a triac 380. Triac 380 is connected between the AC line 304 and the fan motor 346.

When diac 379 is activated, it turns triac 380 "on", causing the AC line voltage 304 to be applied across motor 346 and generating current flow through the motor 346. Current will flow through motor 346 in response to AC line voltage 304 until some time later, when AC line 304 reverses polarity, and the current in motor 346 reduces to zero. When the current in motor 346 reduces to a zero value, triac 380 ceases to conduct, and will remain nonconducting until reactivated by triac 379 in response to a motor control signal applied to transistor 376.

Thus, a motor control signal applied to transistor 376 will cause the AC line voltage 304 to be applied to motor 346 for approximately one-half cycle of the AC line 304. Further application of AC line voltage 304 to motor 346 will be delayed until a motor control signal to transistor 376 reactivates triac 380. The delay time between the end of a half cycle of the AC line 304, and the time of reactivation of triac 380, is used as discussed below to control the total power applied to motor 346.

Specifically, referring now to FIG. 11B, the AC line voltage 304 has a roughly sinusoidal waveform including periodic zero crossings at times represented by lines 390. Through operation of the circuitry described above in FIG. 10B, the zero crossing signal includes a brief pulse to a "0" logic level at each of the zero crossings, and otherwise has a "1" logic level. Microprocessor 300 responds to this zero crossing signal by producing a motor control signal to transistor 376 a time delay after each zero crossing. This time delay, represented by the gap 392 between a zero crossing line 390 and a motor control signal pulse, is varied by microprocessor 300 in a manner to control the total power applied to fan motor 346 to a constant predetermined value.

Specifically, referring to FIG. 11A, microprocessor 300 receives zero crossing signals on line 307, and computes a time delay between these zero crossing signals to determine whether the AC line frequency is 50 Hz or 60 Hz (step 400). Next, microprocessor 300 determines the RMS amplitude of the AC line voltage from the RMS to DC converter 308. This amplitude is used to select an entry in either the 60 Hz lookup table 331 or 50 Hz lookup table 332, depending on whether the AC line frequency is 60 Hz or 50 Hz (step 402). The selected entry in the lookup table 331 or 332 identifies the time delay 392 between each zero crossing and each motor control signal. This off delay is read (step 404) from the lookup table, and then used by microprocessor 300 in producing further motor control signals.

When the fan in the climate controlled incubator is in operation, a substantial amount of electrical energy is consumed, as heat, in the coils of the fan motor. This heat energy affects the climate control of the incubator by acting as a second heater within the incubator. While this source of heat cannot be eliminated, it can be controlled so that the amount of heat produced by fan motor 346 is constant despite variations in line frequency and line voltage. Both the line frequency and the line voltage will affect the response of the fan motor 346 to the AC line voltage through the operation of circuit 344 of FIG. 10C. Specifically, fan motor 346 has a highly reactive electrical impedance, and will produce a motor current which depends upon the frequency applied to the motor, as well as the amplitude. Furthermore, the current drawn by fan motor 346 is related to the amplitude of the AC line voltage in a non-linear fashion.

To compensate for these various effects caused by the non-linear and reactive impedances of fan motor 346, lookup tables 331 and 332 are generated and filled with values for time delay 392. The values stored in the tables 331 and 332 indicate the delay time which, when used with the associated AC line frequency and amplitude, will cause fan motor 346 to produce a predetermined heat output. Lookup tables 331 and 332 are generated by applying various line frequencies and line amplitudes to a fan motor 346, and using the circuit of FIG. 10C to vary the motor control signal pulse time delay 392 while monitoring the RMS voltage appearing across the terminals of the fan motor 346. For each combination of line frequency and amplitude, the time delay 392 is varied until a predetermined desired RMS voltage appears across the terminals of fan motor 346. The time delay which achieves this predetermined RMS voltage is stored in lookup table 331 or 332 in the appropriate location. By filling out lookout tables 331 and 332 in this manner, when microprocessor 300 later retrieves a value from a lookup table 331 or 332, this value will be the appropriate value to control fan motor 346 to generate the desired predetermined amount of heat energy regardless of variations in the AC line frequency and amplitude.

Figure 12:
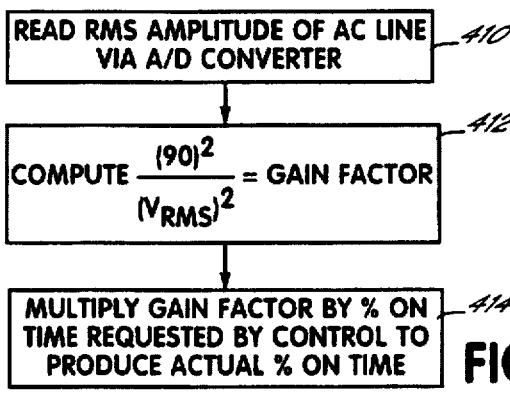
FIG. 12 is a flow chart of operations taken by the microprocessor of FIG. 9 to compensate the heater power consumption for line voltage variations.

Referring now to FIG. 12, a similar compensation is performed in the control of heaters 340 and 342. Heaters 340 and 342 are controlled by microprocessor 300 to produce a desired heat output. Specifically, microprocessor 300 is programmed to implement an adaptive proportional-integral-derivative control algorithm, responsive to temperature readings from temperature sensor 314, to control the temperature inside the incubator. A particular suitable algorithm is the ISA "ideal algorithm for closed loop PID control". This control algorithm generates a value indicative of the heater power that should be applied at any given time to properly control the temperature of the incubator. This heater power is represented by a percentage of maximum heat. Microprocessor 300 controls main heater 340 or secondary heaters 342 to produce the desired percentage of maximum heat, by alternately applying the AC line voltage 304 to the heater coil, such that the duty cycle with which the AC voltage is applied equals the desired percentage of maximum heat.

The heat produced by the heater 340 or 342 is a function not only of the duty cycle created by microprocessor 300, but also of the RMS AC line voltage which is applied to the heater. Although the adaptive control algorithm implemented by microprocessor 300 could over time compensate for different AC line voltages (by self-adjustment of its adaptive parameters), this adaptation could take hours or even days, during which the temperature control of the incubator will be unacceptably out of control. To avoid the need for dynamic adaptation of the control algorithm in microprocessor 300, microprocessor 300 more directly compensates for AC line voltage, to eliminate the potential effects of variation in the RMS AC line voltage applied to the heater 340 or 342.

Specifically, the adaptive control algorithm used by microprocessor 300 is initialized using a 90 volt AC RMS line voltage. Then, the actual AC line voltage is measured and incorporated into the control for heater 340 or 342 to compensate for variations of the AC line voltage away from the nominal 90 volts RMS line voltage used in initializing the adaptive control algorithm.

In this compensation process, microprocessor 300 begins by reading the RMS amplitude of the AC line from circuit 308 via A/D converter 310 (step 410). Next, microprocessor 300 computes the ratio of $90^2$ to the square of the measured RMS voltage (step 402). This ratio is a heat reduction factor indicative of the reduction in duty cycle needed to compensate for additional heat energy that will be produced by the heater due to additional RMS AC line voltage above the nominal 90 volt level used in calibration of the adaptive control algorithm. Accordingly, in step 414, microprocessor 300 multiplies this gain factor by the percent power requested by the adaptive control algorithm to produce the actual heater duty cycle (on-time) percentage to be used in generating heat from heater 340 or 342. In this way, any additional heater power which might have been generated by AC line RMS voltage greater than 90 volts, is compensated by reduction in the on-time of the heater 340 or 342.

Figure 13A:
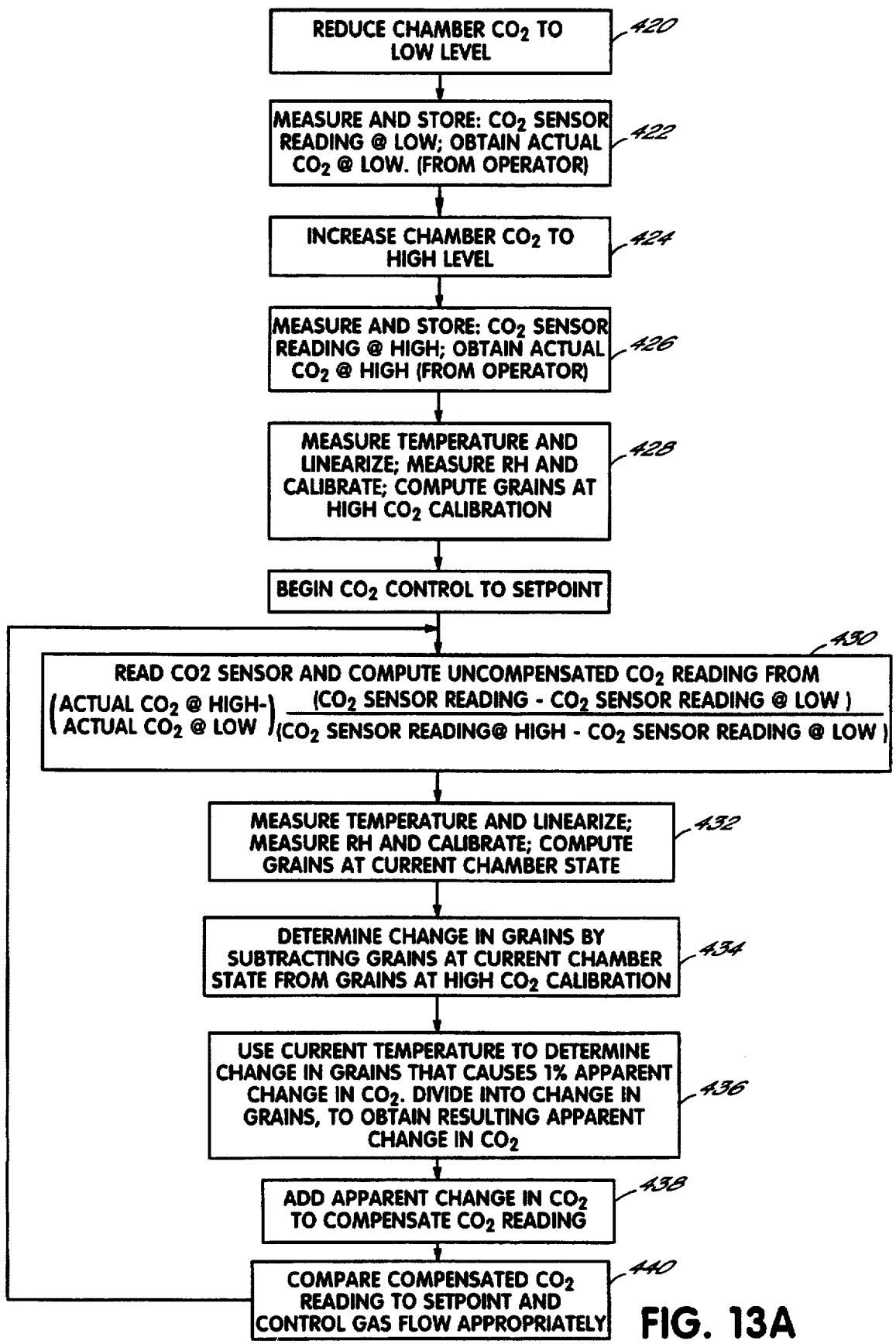
FIG. 13A is a flow chart of operations taken by the microprocessor of FIG. 9 to compensate readings of the $CO_2$ Sensor of FIG. 9 for variations in humidity.

Referring now to FIG. 13A, as discussed above, a thermal conductivity carbon dioxide sensor 312 is compensated for variations caused by humidity and linearized by microprocessor 300. This process is illustrated in FIG. 13A and charted in FIG. 13B.

To initiate this process, the carbon dioxide sensor outputs are measured at low and high levels of $CO_2$ and used to interpolate further signal values. To do so, the carbon dioxide level in the incubator is reduced to a low level (for example by flooding the incubator with ambient room air) (step 420), and then microprocessor 300 measures and stores the carbon dioxide sensor reading at this low carbon dioxide level. At the same time, microprocessor 300 obtains and stores the actual carbon dioxide level (e.g., from operator input) (step 422). Next, the carbon dioxide level in the incubator is increased to a high value (step 424), and microprocessor 300 measures and stores the carbon dioxide sensor reading at this high level and the actual carbon dioxide level (e.g., from operator input) (step 426). While the carbon dioxide level is still at this high value, microprocessor 300 measures the incubator temperature using temperature sensor 314 and the appropriate linearization lookup table 334, and measures the relative humidity using humidity sensor 316 and the conversion lookup table 334, and finally computes the grains (humidity) within the incubator at the time of the high carbon dioxide reading (step 428). At this point, microprocessor 300 is ready to begin carbon dioxide readings and control of carbon dioxide levels in the incubator to a set point.

Each reading obtained from carbon dioxide sensor 312 is compensated by a sequence of steps beginning with step 430 and the following steps. Initially, microprocessor 300 reads the carbon dioxide sensor and then uses a linear interpolation procedure to compute an uncompensated carbon dioxide reading. This linear interpolation procedure determines the relationship between the carbon dioxide sensor reading and the low and high readings obtained in steps 422 and 426. Then, the relationship between the current reading and the low and high readings is used to interpolate a carbon dioxide level based upon the actual carbon dioxide levels at the low and high readings. The specific computation for this step is identified in FIG. 13A, step 430.

After thus determining an uncompensated carbon dioxide reading, microprocessor 300 proceeds to compensate this reading for sensitivities to humidity variation. First (step 432), microprocessor 300 measures the temperature in the incubator using temperature sensor 314 and linearization table 334. Next, microprocessor 300 determines the relative humidity in the incubator using humidity sensor 316 and the conversion table 334. Finally the relative humidity reading is converted to grains using a table for converting a temperature and relative humidity value into a grains value, which table is stored in memory 330 as one of the tables 336.

After this initial preparation, microprocessor 300 proceeds to step 434 in which it determines the change in grains in the incubator by subtracting the grains at the current time from the grains measured in step 428 when the high carbon dioxide sensor reading was taken. This change in grains in the incubator is used to compensate for variations in the carbon dioxide sensor reading. Specifically, in step 436, the current temperature reading is used to determine the change in grains in the incubator that causes a 1% apparent change in the carbon dioxide concentration. This value is multiplied by the actual change in grains from the time of the high carbon dioxide reading to obtain a resulting apparent change in the carbon dioxide reading which is attributable to humidity change (step 436). This apparent change in carbon dioxide reading is then added to the uncompensated carbon dioxide reading to obtain a compensated carbon dioxide reading (step 438). The compensated carbon dioxide reading is then compared to the user-defined set point to control the gas flow into the incubator (step 440).

The steps discussed above can be diagrammed as shown in FIG. 13B. Specifically, the temperature sensor reading at the high carbon dioxide calibration 441 and the relative humidity sensor reading at the high carbon dioxide calibration 442 are processed through a temperature linearization table 334 and relative humidity conversion table 334 to obtain the actual temperature and relative humidity at the high carbon dioxide calibration. The temperature is then passed through a table 336 to obtain the number of grains which correspond to 100% relative humidity at the temperature of high carbon dioxide calibration. Next, the relative humidity is divided by one hundred and multiplied by this value to produce a value 444 corresponding to the grains at the time of the high carbon dioxide calibration.

Later, when a linearized carbon dioxide sensor reading (445) is obtained, the difference between this sensor reading and the linearized sensor reading at low carbon dioxide calibration (446) is computed and this difference is compared to the difference between the linearized carbon dioxide sensor reading at low calibration (446) and the linearized carbon dioxide sensor reading (448) at high calibration. The quotient of these two differences (450) is then multiplied by the difference between the actual carbon dioxide level at the high calibration (452) and the actual carbon dioxide level at low calibration (454). The result (456) is a linearized, uncompensated carbon dioxide reading.

The current relative humidity sensor reading (460) and current temperature sensor reading (462) are processed through a relative humidity conversion table 334 and temperature linearization table 334 to produce current relative humidity and current temperature readings (461, 463). The current temperature reading 463 is then processed through the temperature-relative humidity table 336 to obtain the number (464) of grains that correspond to 100% relative humidity at the current temperature. This value is combined with the current relative humidity (461) to produce a number (465) indicative of the current grains in the incubator. The difference between this number and the grains at the time of high carbon dioxide calibration (444) indicates the change in grains (470) since high carbon dioxide calibration.

The current temperature is passed through a second calibration table 336 to create a value (472) indicating the change in grains that causes a 1% apparent change in carbon dioxide concentration at the current temperature. This value is combined with the change in grains (470) to produce the apparent change in carbon dioxide due to humidity change (474). This value is added to the uncompensated carbon dioxide sensor reading (456) to produce a humidity compensated carbon dioxide reading (476).

In accordance with the foregoing, variations in apparent carbon dioxide readings caused by humidity changes are compensated through the use of the various lookup tables identified.

Lookup table 336 identifying the number of grains that correspond to 100% relative humidity at each given temperature can be generated from tables in any handbook of chemistry and physics indicating theoretical relationships between relative humidity, temperature and grains. The second table 336 for converting a temperature into the change in grains that causes a 1% apparent change in carbon dioxide at that temperature, may be generated by empirical measurements created by varying the humidity, carbon dioxide and temperature levels in a incubator, and measuring carbon dioxide sensor outputs to determine the amount of carbon dioxide sensor variation caused by changes in grains at various temperatures.

Figure 14A:
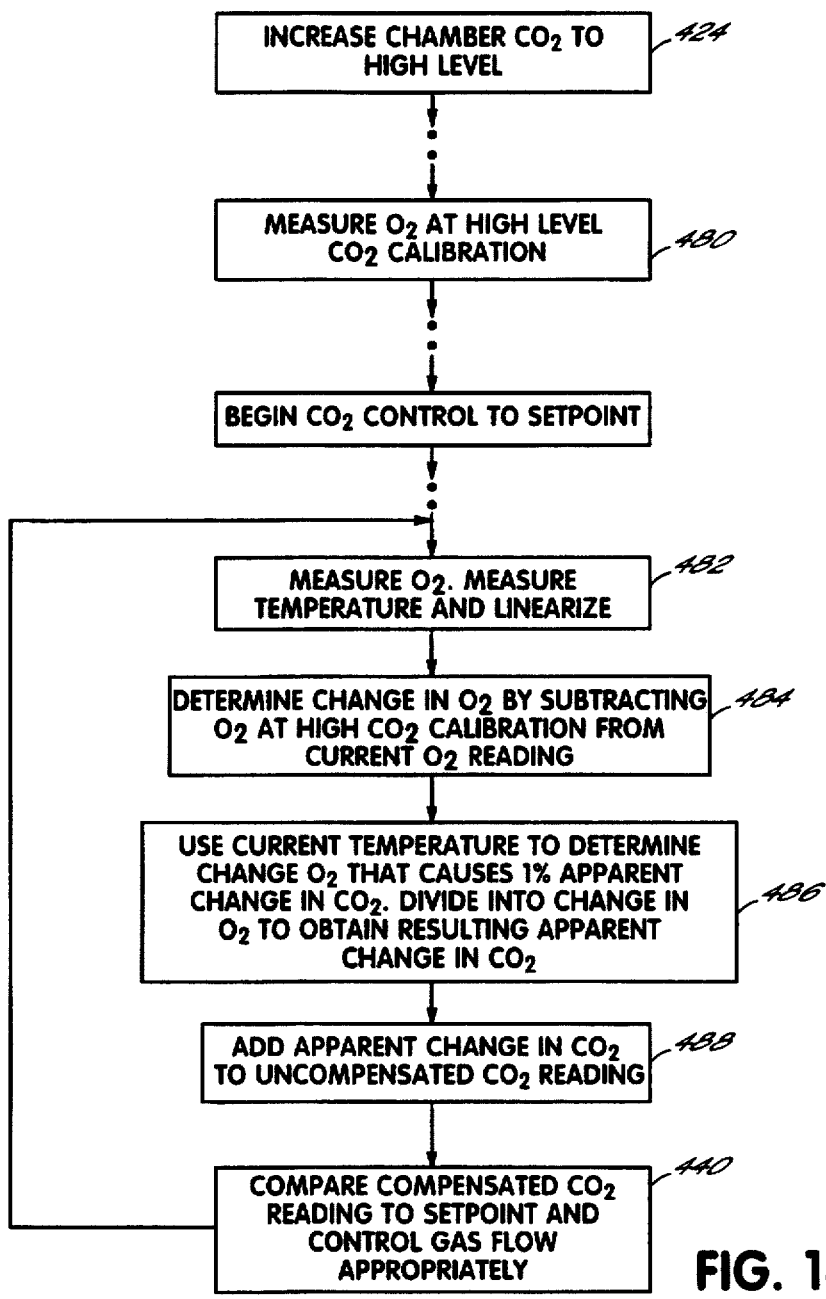
FIG. 14A is a flow chart of operations taken by the microprocessor of FIG. 9 to compensate readings of the $CO_2$ Sensor of FIG. 9 for variations in oxygen.

A similar procedure is used to compensate the carbon dioxide readings for variations in oxygen content within the incubator. Referring to FIG. 14A, this procedure also begins with the calibration of the carbon dioxide sensor. Specifically, after step 424 when the incubator carbon dioxide has been increased to a high level, the oxygen level in the incubator is measured (step 480) and stored for later use in calibration.

Later, the carbon dioxide sensor output is calibrated for oxygen variation by measuring the oxygen level in the incubator and the temperature (and linearizing the temperature reading using a table 334) (step 482). Next, the change in oxygen is determined by subtracting the oxygen level at the high carbon dioxide calibration from the current oxygen reading (step 484). Then, the current temperature is used to determine the change in oxygen that would cause a 1% apparent change in the carbon dioxide reading. This is multiplied by the actual change in oxygen to obtain the resulting apparent change in carbon dioxide (step 486). Finally, this apparent change in carbon dioxide is added to the uncompensated carbon dioxide reading to produce a compensated carbon dioxide reading (step 488). Subsequently, as discussed above, the compensated carbon dioxide reading is compared to the set point, and used to control the gas flow into the incubator as appropriate (step 440).

Figure 14B:
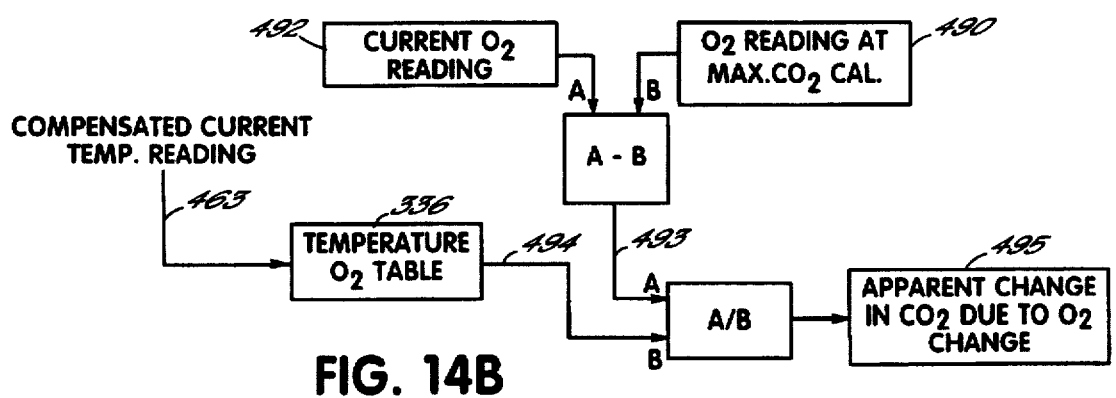
FIG. 14B is a mathematical operation diagram illustrating the method of compensation described in FIG. 14A.

The procedure described above may also be illustrated graphically as seen in FIG. 14B. Specifically, the oxygen reading (490) obtained during high carbon dioxide calibration, is subtracted from the current oxygen reading (492) to obtain a value (493) indicative of the change in oxygen since high carbon dioxide calibration. Next, the linearized current temperature reading (463) is passed through a table 336 to obtain a value (494) indicating the change in oxygen that would cause a 1% apparent change in a carbon dioxide reading at the current temperature. The change in oxygen (493) is then divided by the amount of oxygen change that would cause a 1% apparent change in carbon dioxide (494) to obtain the apparent change in carbon dioxide which is due to changes in the oxygen level (495). This value (495) is then added to the carbon dioxide reading to obtain a compensated carbon dioxide reading.

The above discussed table 336 indicating the change in oxygen that would cause a 1% apparent change in a carbon dioxide reading at various temperatures, may be generated empirically by applying various temperatures oxygen concentrations and carbon dioxide concentrations to a thermal conductivity carbon dioxide sensor, to determine for each temperature, and oxygen concentration change, the amount of apparent carbon dioxide change produced. The resulting values stored in the table 336 can then be used in the manner discussed to produce oxygen level compensation of the carbon dioxide sensor.

Referring now to FIG. 15A, in one embodiment of the invention, an infrared carbon dioxide sensor is used to sense the carbon dioxide levels in the incubator, rather than a thermal conductivity sensor. As noted above, an infrared sensor is more expensive than a thermal conductivity sensor; however, an infrared sensor is not subject to substantial variation as a result of oxygen or humidity.

The infrared sensor is calibrated using zero end span potentiometers which are connected to the infrared sensor at terminals on the sensor. As seen in FIG. 15C, the infrared sensor 500 produces an output signal on line 315, and includes terminals 501 for connection to a potentiometer for adjusting the zero of the sensor output signal on line 315, and terminals 502 for connection to a potentiometer for adjusting the gain or span of the output signal produced on line 315. Sensor 500 also produces a 6 volt source signal on terminal 503 and is responsive to a reference signal on terminal 504 to drive the infrared light source used by the sensor.

In accordance with principles of the present invention, digital potentiometers 506 and 508 are connected to terminals 501 and 502, respectively, to control the zero and span of the output on line 315. Furthermore, the 6 volt source on line 503 produced by the sensor, and a 5 volt source 510, are alternately connected to input terminal 504 as part of the calibration procedure, which is discussed below. The voltage on line 504 and the sensor output signal on line 315 are digitized by the A/D converter 310 and delivered to microprocessor 300.

Microprocessor 300 controls digital potentiometers 506 and 508 and also references stored curves found in a table 336, and a linearization table 334, in memory 330 to calibrate and linearize the infrared sensor output signal on line 315.

The 5 or 6 volt reference signal is alternately applied to input line 504 by attaching a jumper 512 between line 504 and either line 503 or line 505. When the jumper 512 is connected between line 504 and line 505, the 5 volt source 510 is applied to the input terminal 504, resulting in a low level light output from the infrared sensor's internal infrared light source. When jumper 512 is connected between line 504 and line 503, the sensor's internal 6 volt source is applied to the input terminal 504, resulting in a normal, high level light output from the infrared sensor's internal infrared light source. As drawn in FIG. 15C, jumper 512 is positioned to connect the 5 volt source 510 to the sensor's input line 504.

Referring now to FIG. 15A, to calibrate the infrared sensor 500, jumper 512 is initially positioned between lines 503 and 504, to connect the normal 6 volt source to terminal 504. The calibration procedure followed by microprocessor 300 begins at step 520 by waiting until the normal source voltage is sensed on terminal 504. A/D converter is used to determine the approximate voltage on line 504 and processing continues to step 522 only when an approximately 6 volt voltage is detected on line 504.

Once the normal source voltage is applied to the infrared sensor 500, in step 522 microprocessor 300 controls the incubator to expose the infrared sensor to room air, which is 0.033% carbon dioxide, so that the infrared sensor is exposed to a known, predetermined carbon dioxide concentration. Once the sensor has been sufficiently exposed to room air, microprocessor 300 adjusts the digital potentiometer 506, to change the infrared sensor output until it has an output value of zero (step 524). This establishes the zero setting for the infrared sensor 500 such that a room air carbon dioxide concentration produces a zero output on line 315.

Next, in step 526, microprocessor 300 waits until a reduced source voltage of approximately 5 volts is applied to input line 504 of sensor 500. To do this, the user must move jumper 512 to the position shown in FIG. 15C. Only when microprocessor 300 detects a roughly 5 volt voltage on line 504, it will proceed to step 528.

In step 528, microprocessor 300 retrieves from memory 330 a stored curve from a table 336. As illustrated in FIG. 15B, this table stores a number of curves 529. Each of these curves indicates the sensor output as a function of infrared source voltage when the sensor is exposed to ambient air having a carbon dioxide concentration of 0.033%. In step 528, microprocessor 300 locates the curve 529 which has zero sensor output voltage at the source voltage detected on line 504 in step 520. This curve describes the state of operation of the infrared sensor 500.

In step 530, microprocessor 300 uses the retrieved curve to predict the sensor output which should be produced by the approximately 5 volt source voltage produced by source 510, and which is currently being applied to line 504. In step 532, microprocessor 300 adjusts potentiometer 508 to change the infrared sensor output voltage on line 315 until the sensor output voltage is equal to the predicted voltage. By doing so, microprocessor 300 adjusts the gain in the infrared sensor to normalize the behavior of the infrared sensor to the selected curve 529.

After thus setting the gain (span) of the infrared sensor, microprocessor 300 again waits in step 534 until the normal source voltage is reapplied to source voltage terminal 504 of infrared sensor 500. During this waiting time, the operator must move the jumper 512 from the position shown in FIG. 15C to the position shown in dotted outline in FIG. 15C. Once the jumper has been moved, and microprocessor 300 detects a normal source voltage applied to terminal 504, microprocessor 300 moves to step 536, and (if necessary) readjusts potentiometer 506 to change the infrared sensor output to produce a zero output. This second readjustment of potentiometer 506 eliminates possible zeroing errors produced during adjustments of potentiometer 508.

After this calibration procedure has been completed, microprocessor 300 has adjusted the infrared sensor into calibration, such that the sensor output 315 can subsequently be used to measure carbon dioxide, by retrieving the sensor output voltage 315 via A/D converter 310 and linearizing the output voltage using a linearization table 334 stored in memory 330, as discussed above.

It will be noted that the above-described calibration procedure does not require altering the carbon dioxide concentration in the incubator, but rather merely involves applying room air to the carbon dioxide sensor. Known carbon dioxide sensor calibration procedures require exposing the sensor to different carbon dioxide concentrations, which is not only time consuming but also consumes resources of carbon dioxide gas. The above-described procedure is thus highly advantageous as compared to these known procedures.

While preferred embodiments of the various aspects of the invention have been described in detail, those of ordinary skill will recognize modifications thereof still falling within the spirit and scope of the inventive concepts.

What is claimed is:

1. A controlled atmosphere incubator comprising:

a cabinet including a chamber surrounded by top, bottom, rear and side walls and having a front side with an opening;

an outer door pivotally mounted to said front side;

an inner glass door pivotally mounted to said front side by at least one hinge and disposed inside of said outer door for sealing said opening during incubation procedures, said inner glass door including a clear, electrically conductive and heat generating coating on a surface thereof, said coating being operatively connected to a control for selectively passing current through said coating to heat said inner glass door;

a flexible gasket removably secured to said cabinet about said opening, said gasket including a mounting portion having elements for frictionally engaging said cabinet to allow selective application and removal of said gasket with respect to said cabinet and a feather portion extending from said mounting portion for engaging said inner door and creating a seal between said chamber and said inner door;

a water jacket contained in said top, bottom, rear and side walls and in said front side surrounding said opening;

a heater in thermal communication with said water jacket;

fastener receiving elements secured on the left and right of said front side and extending into the water jacket contained in said front side, said fastener receiving elements secured in a liquid tight manner for preventing escape of water from said water jacket;

fasteners removably securing said hinge to said fastener receiving elements on one of the left and right sides of said front side;

a blower mounted within said chamber and including an inlet and an outlet;

a plenum formed in said chamber and providing an air circulation path through said chamber, said plenum being partially formed by a plate mounted across said chamber and between the inlet and outlet of said blower;

a blower mounted within said chamber and including an inlet and an outlet for circulating air within said chamber;

an ambient air inlet connected between ambient and the inlet to said blower; and a chamber air outlet connected between said chamber and ambient.

2. A controlled atmosphere incubator comprising:

a cabinet including a chamber surrounded by top, bottom, rear and side walls and having a front side with an opening;

a heater in thermal communication with said chamber;

an outer door pivotally mounted to said front side;

a dual pane inner glass door having a spacer disposed between an inner pane and an outer pane to create an air gap, said inner glass door pivotally mounted to said front side by at least one hinge and disposed inside of said outer door for sealing said opening during incubation procedures, said inner glass door including a clear, electrically conductive and heat generating coating on a surface thereof facing said air gap, said coating being operatively connected to a control for selectively passing current through said coating to heat said inner glass door;

a pair of silk screened bus bars formed in contact with a respective pair of outer edge portions of said coating; and wherein the surface having said coating includes a perimeter edge portion void of said coating and said spacer is formed of a metal material contacting said perimeter edge portion.

3. The controlled atmosphere incubator of claim 2 wherein said inner and outer panes are mounted within a surrounding frame structure, said frame having at least one channel for allowing electrical connections to be made to said bus bars.

4. The controlled atmosphere incubator of claim 2 further comprising first and second alternatively usable electrical connectors respectively mounted to upper and lower edge portions of said inner glass door for electrically connecting said bus bars to a control.

5. The controlled atmosphere incubator of claim 2 wherein the surface having said coating is the surface of said inner pane facing said air gap.

6. A controlled atmosphere incubator comprising:

a cabinet including a chamber surrounded by top, bottom, rear and side walls and having a front side with an opening;

a heater in thermal communication with said chamber;

an outer door pivotally mounted to said front side;

an inner door pivotally mounted to said front side and disposed inside of said outer door for sealing said opening during incubation procedures; and a flexible gasket removably secured to said cabinet about said opening, said gasket including a mounting portion having elements for frictionally engaging said cabinet to allow selective application and removal of said gasket with respect to said cabinet and a feather portion extending from said mounting portion for engaging said inner door and creating a seal between said chamber and said inner door, wherein said mounting portion conforms to curved corners of said opening by flexing out of an approximate bending plane and said feather portion includes an outer edge lying on a side of said bending plane closer to an open end of said U-shaped portion.

7. The controlled atmosphere incubator of claim 6 wherein said mounting portion includes a generally U-shaped portion and the elements for frictionally engaging said cabinet include projections extending inwardly from said U-shaped portion.

8. The controlled atmosphere incubator of claim 6 wherein said feather portion is angled away from the open end of said U-shaped portion.

9. The controlled atmosphere incubator of claim 8 wherein said angle is approximately 80°.

10. A controlled atmosphere incubator comprising:

a cabinet including a chamber surrounded by top, bottom, rear and side walls and having a front side with an opening;

a water jacket contained in said top, bottom, rear and side walls and in said front side surrounding said opening;

a heater in thermal communication with said water jacket;

an outer door pivotally mounted to said front side;

an inner door pivotally mounted to said front side by at least one hinge and disposed inside of said outer door for sealing said opening during incubation procedures;

fastener receiving elements secured on the left and right of said front side and extending into the water jacket contained in said front side, said fastener receiving elements secured in a liquid tight manner for preventing escape of water from said water jacket; and fasteners removably securing said hinge to said fastener receiving elements on one of the left and right sides of said front side.

11. The controlled atmosphere incubator of claim 10 wherein said inner door includes an electric heater thereon and upper and lower edges of said inner door each include electrical connectors with one of said connectors being used to connect said electric heater to a control when said hinge is secured to the left of the front side and the other of said connectors being used to connect said electric heater to said control when said hinge is fastened to the right of the front side.

12. The controlled atmosphere incubator of claim 10 wherein the fastener receiving elements and the front side of said incubator include mating stop surfaces which prevent rotation of said fastener receiving elements when said fasteners are secured thereto.

13. The controlled atmosphere incubator of claim 12 wherein an O-ring seal is disposed between each fastener receiving element and an opening through said front side which receives said fastener receiving element.

14. A controlled atmosphere incubator comprising:

a heater;

a cabinet including a chamber in thermal communication with the heaters and surrounded by top, bottom, rear and side walls and having a front side with an opening;

an outer door pivotally mounted to said front side;

a blower mounted within said chamber and including an inlet and an outlet;

a plenum formed in said chamber and providing an air circulation path through said chamber, said plenum being partially formed by a plate mounted across said chamber and between the inlet and outlet of said blower; and a HEPA filter removably attached to the inlet of said blower and contained within said chamber.

15. The controlled atmosphere incubator of claim 14 wherein said plate is mounted adjacent an upper wall of said chamber to form said plenum between said plate and said upper wall.

16. The controlled atmosphere incubator of claim 15 wherein said inlet extends below said plate and said HEPA filter is mounted adjacent to a lower surface of said plate.

17. The controlled atmosphere incubator of claim 14 further comprising an ambient air inlet connected between the ambient and the inlet of said blower and a chamber air outlet leading from the chamber to the ambient.

18. The controlled atmosphere incubator of claim 17 wherein said ambient air inlet and said chamber air outlet include HEPA filters.

19. A controlled atmosphere incubator comprising:

a cabinet including a chamber surrounded by top, bottom, front, rear and side walls, one of said sides having an opening for accessing said chamber;

an outer door mounted to said one side;

a source of humidity in communication with the chamber;

a heater in thermal communication with the chamber;

a blower operatively connected to said chamber and including an inlet and an outlet for circulating air within said chamber; and a humidity control including an ambient air inlet conduit communicating between ambient and the inlet to said blower and a chamber air outlet connected between said chamber and ambient.

20. The controlled atmosphere incubator of claim 19 wherein filters are mounted to said ambient air inlet and said chamber air outlet to filter passing through said ambient air inlet and said chamber air outlet.

21. The controlled atmosphere incubator of claim 20 wherein said filters are HEPA filters.

22. A controlled atmosphere incubator comprising:

a heater;

a cabinet including a chamber in thermal communication with the heater and surrounded by top, bottom, rear and side walls and having a front side with an opening;

a door pivotally mounted to said front side to allow access to the chamber through the opening;

a blower operatively connected to said chamber and including an inlet and an outlet for circulating air within said chamber; and a HEPA filter removably mounted within said chamber and operatively connected to the blower to filter the air being circulated within the chamber.

* * * * *

UNITED STATES PATENT AND TRADEMARK OFFICE
CERTIFICATE OF CORRECTION

PATENT NO. : 5,792,427

DATED : August 11, 1998

INVENTOR(S) : Mark A. Hugh

It is certified that error appears in the above-identified patent and that said Letters Patent is hereby corrected as shown below:

On the title page, at [75], delete "David V. Lohr, Beverly; Peter J. Borton, Marietta, all of Ohio".

Claim 6, column 21, line 65, change "mounting" to --U-shaped--.

Claim 7, column 22, lines 11-12, delete "said mounting portion includes a generally U-shaped portion and".

Signed and Sealed this

Twenty-fifth Day of May, 1999

Attest:

Q. TODD DICKINSON

Attesting Officer

Acting Commissioner of Patents and Trademarks